United States Patent
Blume et al.

(10) Patent No.: US 6,528,082 B2
(45) Date of Patent: *Mar. 4, 2003

(54) METHODS AND PHARMACEUTICAL COMPOSITIONS EMPLOYING DESMETHYLSELEGILINE TO TREAT NEOPLASTIC DISEASES OR CONDITIONS

(75) Inventors: Cheryl D. Blume, Tampa, FL (US); Anthony R. DiSanto, Dade City, FL (US)

(73) Assignee: Somerset Pharmaceuticals, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/940,252

(22) Filed: Aug. 27, 2001

(65) Prior Publication Data

US 2002/0037930 A1 Mar. 28, 2002

Related U.S. Application Data

(63) Continuation-in-part of application No. 08/679,328, filed on Jul. 12, 1996, now Pat. No. 6,033,682, which is a continuation-in-part of application No. 08/679,330, filed on Jul. 12, 1996, now Pat. No. 6,348,208, which is a continuation-in-part of application No. PCT/US96/01568, filed on Jan. 11, 1996, which is a continuation-in-part of application No. 08/372,139, filed on Jan. 13, 1995, now abandoned.

(60) Provisional application No. 60/228,431, filed on Aug. 28, 2000, and provisional application No. 60/001,979, filed on Jul. 31, 1995.

(51) Int. Cl.$^7$ ................................................. A61F 13/00
(52) U.S. Cl. ..................... 424/434; 424/400; 424/436; 424/448; 424/435; 424/422; 424/449; 514/654
(58) Field of Search ......................... 424/400, 422, 424/436, 434, 435, 441, 448; 514/654

(56) References Cited

U.S. PATENT DOCUMENTS

| | | | |
|---|---|---|---|
| 6,033,682 A | 3/2000 | DiSanto | 424/434 |
| 6,210,706 B1 | 4/2001 | DiSanto | 424/449 |
| 6,299,901 B1 * | 10/2001 | Di Santo et al. | 424/449 |
| 6,348,208 B1 * | 2/2002 | Blume et al. | 424/449 |

FOREIGN PATENT DOCUMENTS

| | | |
|---|---|---|
| WO | 99/18946 | 4/1990 |
| WO | 96/22068 | 7/1996 |
| WO | 99/36076 | 7/1999 |
| WO | 99/40908 | 8/1999 |
| WO | 99/47133 | 9/1999 |
| WO | 00/71109 | 11/2000 |

OTHER PUBLICATIONS

Borbe, et al., "Kinetic Evaluation of MAO–B–Activity Following Oral Administration of Selegiline and Desmethyl–Selegiline in the Rat," *J. Neural. Transm.* 32:131–137 [Suppl.](1990).

Gershon, et al., "Monoamine Oxidase Inhibition and the Induction of Ponto–Geniculo–Occipital Wave Activity by Reserpine in the Cat," *J. Pharmacol. Exp. Ther.*, 197(3):556–566 (1976).

(List continued on next page.)

*Primary Examiner*—Thurman K. Page
*Assistant Examiner*—Lakshmi Channavajjala
(74) *Attorney, Agent, or Firm*—Vinson & Elkins L.L.P.

(57) ABSTRACT

The application is directed to the treatment of neoplastic diseases or conditions by administering R(–) desmethylselegiline, S(+) desmethylselegiline, or a combination of the two. Neoplastic diseases and conditions responsive to R(–) desmethylselegiline and/or S(+) desmethylselegiline include both malignant and benign neoplasms.

26 Claims, 11 Drawing Sheets

TIME (MIN.)

OTHER PUBLICATIONS

Heinonen, et al., "Pharmacokinetic Aspects of L–Deprenyl (Selegiline) and Its Metabolites," *Clin. Pharmacol. Ther.*, 56(6Pt2):742–749 (Dec. 1994).

Heinonen, et al., "Desmethylselegiline, a Metabolite of Selegiline, Is an Irreversible Inhibitor of MAO–B in Human Subjects," *Neurology*, 43(4) Suppl. 2:A156 (Apr. 1993).

Heinonen, et al., "Pharmacokinetics and Metabolism of Selegiline," *Acta Neurol. Scand.*, 126:93–99 (1989).

Martin, et al., "Regression Analysis of the Relationship between Physical Properties and the In Vitro Inhibition of Monoamine Oxidase by Propynylamines," *J. Med. Chem.*, 18(9):883–888 (1975).

MohanKumar, et al., "Deprenyl Stimulates the Release of Luteinizing Hormone from the Pituitary In Vitro," *Life Sciences*, 60(18):1783–1788 (1997).

Nickel, et al., "Effect of Selegiline and Desmethyl–Selegiline on Cortical Electric Activity in Rats," *J. Neural. Transm.*, 32:139–144 (1990).

Reusch, et al., "The Efficacy of L–Deprenyl in Dogs with Pituitary–Dependent Hyperadrenocorticism," *Journal of Veterinary Internal Medicine/American College of Veterinary Internal Medicine*, 13(4) (Jul. 1999).

Szende, et al., "Apoptotic and Antiapoptotic Effect of (–)Deprenyl and (–)–Desmethylselegiline–Deprenyl on Human Cell Lines," *Neurobiology*, 8(3–4):249–255 (2000).

Tatton, et al., "Modulation of Gene Expression Rather Than Monoamine Oxidase Inhibition: (–)–Deprenyl–Related Compounds in Controlling Neurodegeneration," *Neurology*, 47(6) Suppl. 3: S171–S183 (1996).

Williams, et al., "Biochemical and Behavioral Studies of Monoamine Oxidase Inhibition," *Ir. J. Med. Sci.*, 147(1):71–74 (1978).

International Search Report dated Aug. 28, 2002.

Bergstrom, et al., "Differentiation of Pituitary Adenoma and Meningioma: Visualization with Positron Emission Tomography and [$^{11}$C]–L–Deprenyl," *Neurosurgery* 30(6):855–861 (1992).

Czub, et al., "Effects of Selegiline in a Retroviral Rat Model for Neurodegenerative Disease," *Journal of NeuroVirology* 5:458–464 (1999).

Lai and Yu, "R(–)–Deprenyl Potentiates Dopamine–Induced Cytotoxicity Toward Catecholaminergic Neuroblastoma SH–SY5Y Cells," *Toxicology and Applied Pharmacology* 142:186–191 (1997).

Magyar, et al., "The Neuroprotective and Neuronal Rescue Effects of (–)–Deprenyl," *J. Neural Transm.* [Suppl.] 52:109–123 (1998).

Maruyama, et al., "(–)–Deprenyl Protects Human Dopaminergic Neuroblastoma SH–SY5Y Cells from Apoptosis Induced by Peroxynitrite and Nitric Oxide," *J. Neurochem.*, 70(6):2510–2515 (1998).

Maruyama and Naoi, "Neuroprotection by (–)–Deprenyl and Related Compounds," *Mechanisms of Ageing and Development* 111:189–200 (1999).

Minami, et al., "Generation of Reactive Oxygen Species Amounts for Cytotoxicity of an Endogenous Dopaminergic Neurotoxin, (R)–N–Methylsalsolinol, to Differentiated Dopaminergic SH–SY5Y Cells," *J. Neural. Transm.* 105:397–405 (1998).

Pardo, et al., "Ascorbic Acid Protects Against Levodopa–Induced Neurotoxicity on a Catecholamine–Rich Human Neuroblastoma Cell Line," *Movement Disorders* 8(3):278–284 (1993).

Sarabia and Liehr, "Induction of Monoamine Oxidase B by 17β–Estradiol in the Hamster Kidney Preceding Carcinogenesis," *Archives of Biochemistry and Biophysics* [Article No. BB98–727] 355(2):249–253 (Jul. 15, 1998).

Thyagarajan, et al., "Deprenyl Reinitiates Estrous Cycles, Reduces Serum Prolactin, and Decreases the Incidence of Mammary and Pituitary Tumors in Old Acyclic Rats," *Endocrinology* 136(3):1103–1110 (1995).

ThyagaRajan, et al., "Antitumor Effect of L–Deprenyl in Rats with Carcinogen–Induced Mammary Tumors," *Cancer Letters* 123:177–183 (1998).

ThyagaRajan, et al., "L–Deprenyl–Induced Increase in IL–2 and NK Cell Activity Accompanies Restoration of Noradrenergic Nerve Fibers in the Spleens of Old F344 Rats," *Journal of Neuroimmunology* 92:9–21 (1998).

ThyagaRajan, et al., "Effects of L–Deprenyl Treatment on Noradrenergic Innervation and Immune Reactivity in Lymphoid Organs of Young F344 Rats," *Journal of Neuroimmunology* 96:57–65 (1999).

ThyagaRajan and Quadri, "L–Deprenyl Stimulates the Release of Catecholamines in the Rat Medial Basal Hypothalamus in Vivo," 270:79–82 (1999).

ThyagaRajan and Quadri, "L–Deprenyl Inhibits Tumor Growth, Reduces Serum Prolactin, and Suppresses Brain Monoamine Metabolism in Rats with Carcinogen–Induced Mammary Tumors," *Endocrine* 10(3):225–232 (Jun. 1999).

ThyagaRajan, et al., "Anti–Tumor Effect of L–Deprenyl is Associated with Enhanced Central and Peripheral Neurotransmission and Immune Reactivity in Rats with Carcinogen–Induced Mammary Tumors," *Journal of Neuroimmunology* 109:95–104 (2000).

ThygaRajan, et al., "Inhibition of Tumor Growth by L–Deprenyl Involves Neural–Immune Interactions in Rats with Spontaneously Developing Mammary Tumors," *Anticancer Research* 19:5023–5028 (1999).

U.S. patent application Ser. No. 08/679,330 entitled *Methods and Pharmaceutical Compositions Employing Desmethylselegiline* by Cheryl D. Blume et al. filed Jul. 12, 1996.

* cited by examiner

METHODS AND PHARMACEUTICAL COMPOSITIONS EMPLOYING DESMETHYLSELEGILINE TO TREAT NEOPLASTIC DISEASES OR CONDITIONS

This application claims benefit of Ser. No. 60/228,431 filed Aug. 28, 2000 and is a continuation-in-part of Ser. No. 08/679,323 filed Jul. 12, 1996, now U.S. Pat. No. 6,033,682, which is a continuation-in-part of Ser. No. 08/679,330, filed Jul. 12, 1996, U.S. Pat. No. 6,348,208, which is a continuation-in-part of PCT/US96/01561, filed Jan. 11, 1996, and claims benefit of Ser. No. 60/001,927, filed Jul. 7, 1998 and is a continuation-in-part of Ser. No. 08/372,139, filed Jan. 13, 1995, now abandoned.

STATEMENT REGARDING FEDERALLY SPONSORED RESEARCH OR DEVELOPMENT

Not applicable.

REFERENCE TO A "MICROFICHE APPENDIX"

Not Applicable

BACKGROUND OF THE INVENTION

1. Field of the Invention

The present invention pertains to methods and pharmaceutical compositions for using the selegiline metabolite R(−) desmethylselegiline (also referred to simply as "desmethylselegiline" or "R(−)DMS") alone; its enantiomer ent-desmethylselegiline (also referred to as "S(+) desmethylselegiline" or "S(+)DMS") alone; or a combination, such as, for example, a racemic mixture, of the two enantiomers. In particular, the present invention provides compositions and methods for using these agents in the treatment of selegiline-responsive diseases and conditions, particularly diseases or conditions involving neoplastic cells, such as cancerous cells, or those cells that proliferate for no physiologically advantageous purpose.

2. Description of Related Art

Two distinct monoamine oxidase enzymes are known in the art: monoamine oxidase A (MAO-A) and monoamine oxidase B (MAO-B). The cDNAs encoding these enzymes show different promoter regions and distinct exon portions, indicating they are encoded independently at different gene positions. In addition, analysis of the two proteins has shown differences in their respective amino acid sequences.

The first compound found to selectively inhibit MAO-B was (R)-N-α-dimethyl-N-2-propynylbenzeethanamine, also known as L-(−)-N-α-N-2-propynylphenethylamine, (−)-deprenil, L-(−)-deprenil, R-(−)-deprenyl, or selegiline. Selegiline has the following structural formula:

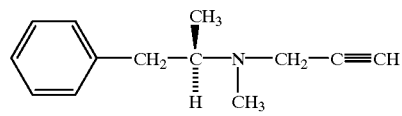

Selegiline is the active ingredient of a human drug product and is known in the art as a component of a therapeutic package. In particular, see Physicians Desk Reference (1995) pp. 2430–2432 (1995 PDR), describing Eldepryl® Tablets, manufactured by Somerset Pharmaceutical, Inc. and marketed by Sandoz, the active ingredient of which is selegiline. For example, the 1995 PDR describes a 5 mg selegiline hydrochloride tablet and further describes the manner in which selegiline-containing therapeutic packages are supplied for commercial use or sale. In particular, the 1995 PDR discloses that 5.0 mg Eldepryl Tablets are sold in "NDC 39506-011-25 bottles of 60 tablets."

In commercial use, selegiline-containing therapeutic packages are labeled and otherwise indicated for use in Parkinsonian patients receiving levodopa/carbidopa therapy. The 1995 PDR cited above provides an example of the complete approved labeling that is employed in known therapeutic packages. Accordingly, known in the prior art are therapeutic packages providing one or more unit doses of selegiline as an active ingredient thereof, supplied in a finished pharmaceutical container that contains said unit doses, and further contains or comprises labeling directing the use of said package in the treatment of a human disease or condition as described above.

In addition to Parkinson's disease, other diseases and conditions for which selegiline is disclosed as being useful include: drug withdrawal (WO 92/21333, including withdrawal from psychostimulants, opiates, narcotics, and barbiturates); depression (U.S. Pat. No. 4,861,800); Alzheimer's disease and Parkinson's disease, particularly through the use of transdermal dosage forms, including ointments, creams and patches; macular degeneration (U.S. Pat. No. 5,242,950); age-dependent degeneracies, including renal function and cognitive function as evidenced by spatial learning ability (U.S. Pat. No. 5,151,449); pituitary-dependent Cushing's disease in humans and nonhumans (U.S. Pat. No. 5,192,808); immune system dysfunction in both humans (U.S. Pat. No. 5,387,615) and animals (U.S. Pat. No. 5,276,057); age-dependent weight loss in mammals (U.S. Pat. No. 5,225,446); schizophrenia (U.S. Pat. No. 5,151,419); and various neoplastic conditions including cancers, such as mammary and pituitary cancers (see, e.g., Thyagarajan et al. (1995)). PCT published application WO 92/17169 discloses the use of selegiline in the treatment of neuromuscular and neurodegenerative disease and in the treatment of CNS injury due to hypoxia, hypoglycemia, ischemic stroke or trauma. In addition, the biochemical effects of selegiline on neuronal cells have been extensively studied (e.g., see Tatton, et al., "Selegiline Can Mediate Neuronal Rescue Rather than Neuronal Protection," *Movement Disorders* 8 (Supp. 1):S20–S30(1993); Tatton, et al., "Rescue of Dying Neurons," *J. Neurosci. Res.* 30:666–672 (1991); and Tatton, et al., "(−)-Deprenyl Prevents Mitochondrial Depolarization and Reduces Cell Death in Trophically-Deprived Cells," 11*th Int'l Symp. on Parkinson's Disease*, Rome, Italy, March 26–30, 1994.)

Selegiline is known to be useful when administered to a subject through a wide variety of routes of administration and dosage forms. For example U.S. Pat. No. 4,812,481 (Degussa AG) discloses the use of concomitant selegiline-amantadine in oral, peroral, enteral, pulmonary, rectal, nasal, vaginal, lingual, intravenous, intraarterial, intracardial, intramuscular, intraperitoneal, intracutaneous, and subcutaneous formulations. U.S. Pat. No. 5,192,550 (Alza Corporation) describes a dosage form comprising an outer wall impermeable to selegiline but permeable to external fluids. This dosage form may have applicability for the oral, sublingual or buccal administration of selegiline. Similarly, U.S. Pat. No. 5,387,615 discloses a variety of selegiline compositions, including tablets, pills, capsules, powders, aerosols, suppositories, skin patches, parenterals, and oral liquids, including oil-aqueous suspensions, solutions, and emulsions. Also disclosed are selegiline-containing sustained release (long acting) formulations and devices.

Although a highly potent and selective MAO-B inhibitor, selegiline's practical use is circumscribed by its dosedependent specificity for MAO-B, and the adverse pharmacology of selegiline metabolites generated after administration.

The selectivity of selegiline in the inhibition of MAO-B is important to its safety profile following oral administration. Inhibition of MAO-A in peripheral sites (such as, for example, gastric epithelium, liver parenchyma, and sympathetic neurons) may cause toxic side effects by interfering with the metabolism of tyramine. Tyramine is normally metabolized in the gastrointestinal tract by MAO-A but when MAO-A is inhibited, tyramine absorption is increased following consumption of tyramine-containing foods such as cheese, beer, herring, etc. This results in the release of catecholamines which can precipitate a hypertensive reaction, producing the "cheese effect." This effect is characterized by Goodman and Gilman as the most serious toxic effect associated with MAO-A inhibitors.

Selegiline is metabolized into its N-desmethyl analog (and their various potentially harmful methamphetamines). Structurally, this N-desmethyl metabolite is the R(-) enantiomeric form R(-)DMS of a secondary amine of the formula:

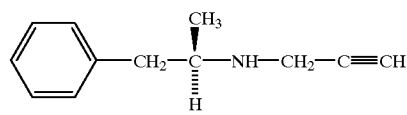

Heretofore, R(-)DMS was not known to have pharmaceutically useful MAO-related effects, i.e., potent and selective inhibitory effects on MAO-B. In the course of determining the usefulness of R(-)DMS for the purposes of the present invention, the MAO-related effects of R(-)DMS were more completely characterized. This characterization has established that desmethylselegiline has exceedingly weak MAO-B inhibitory effects and no advantages in selectivity with respect to MAO-B compared to selegiline.

For example, the present characterization established that selegiline has an $IC_{50}$ value against MAO-B in human platelets of $5 \times 10^{-9}$ M whereas R(-)DMS has an $IC_{50}$ value of $4 \times 10^{-7}$ M, indicating the latter is approximately 80 times less potent as an MAO-B inhibitor than the former. Similar characteristics can be seen in the following data measuring inhibition of MAO-B and MAO-A in rat cortex mitochondrial-rich fractions:

TABLE 1

Inhibition of MAO by Selegiline and Desmethylselegiline

| | Percent Inhibition | | | |
|---|---|---|---|---|
| | Selegiline | | R(-) desmethylselegiline | |
| Conc. | MAO-B | MAO-A | MAO-B | MAO-A |
| 0.003 µM | 16.70 | — | 3.40 | — |
| 0.010 µM | 40.20 | — | 7.50 | — |
| 0.030 µM | 64.70 | 0 | 4.60 | — |
| 0.100 µM | 91.80 | — | 6.70 | — |
| 0.300 µM | 94.55 | 9.75 | 26.15 | 0.0 |
| 1.000 µM | 95.65 | 32.55 | 54.73 | 0.70 |
| 3.000 µM | 98.10 | 65.50 | 86.27 | 4.10 |
| 10.000 µM | — | 97.75 | 95.15 | 11.75 |
| 30.000 µM | — | — | 97.05 | — |
| 100.000 µM | — | — | — | 56.10 |

As is apparent from the above table, selegiline is approximately 128 times more potent as an inhibitor of MAO-B relative to MAO-A, whereas R(-)DMS is about 97 times more potent as an inhibitor of MAO-B relative to MAO-A. Accordingly, R(-)DMS appears to have an approximately equal selectivity for MAO-B compared to MAO-A as-selegiline, albeit with a substantially reduced potency.

Analogous results are obtained in rat brain tissue. Selegiline exhibits an $IC_{50}$, for MAO-B of $0.11 \times 10^{-7}$ M whereas R(-)DMS has an $IC_{50}$ value of $7.3 \times 10^{-7}$ M, indicating R(-)DMS is approximately 70 times less potent as an MAO-B inhibitor than selegiline. Both compounds exhibit low potency in inhibiting MAO-A in rat brain tissue, $0.18 \times 10^{-5}$ for selegiline, $7.0 \times 10^{-5}$ for R(-)DMS. Thus, in vitro R(-)DMS is approximately 39 times less potent than selegiline in inhibiting MAO-A.

Based on its pharmacological profile as set forth above, R(-)DMS as an MAO-B inhibitor provides no advantages in either potency or selectivity compared to selegiline. Indeed, the above in vitro data suggest that use of R(-)DMS as an MAO-B inhibitor requires on the order of 70 times the amount of selegiline.

The potency of R(-)DMS as an MAO-B inhibitor in vivo has been reported by Heinonen, E. H., et al. ("[R(-) Desmethylselegiline, a metabolite of selegiline, is an irreversible inhibitor of MAO-B in human subjects," referenced in Academic Dissertation "Selegiline in the Treatment of Parkinson's Disease," from Research Reports from the Department of Neurology, University of Turku, Turku, Finland, No. 33 (1995), pp. 59–61). According to Heinonen, R(-)DMS in vivo has only about one-fifth the MAO-B inhibitory effect of selegiline, i.e., a dose of 10 mg of desmethylselegiline would be required for the same MAO-B effect as 1.8 mg of selegiline. In rats, Borbe reported R(-)DMS to be an irreversible inhibitor of MAO-B, with a potency about 60 fold lower than selegiline in vitro and about 3 fold lower ex vivo (Barbe, H. O., *J Neural Trans. (Suppl.)*:32:131 (1990)). Thus, all previous investigators have reported data indicating that R(-)DMS is a less-preferred, less effective MAO inhibitor than selegiline and therefore a less desirable therapeutic compound.

BRIEF SUMMARY OF THE INVENTION

The present invention is based upon the surprising discovery that R(-)DMS and its enantiomer S(+)DMS, having the following structure:

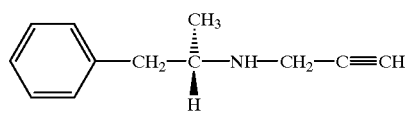

are particularly useful in providing selegiline-like effects in subjects, notwithstanding dramatically reduced MAO-B inhibitory activity and an apparent lack of enhanced selectivity for MAO-B compared to selegiline. It has been discovered that R(-)DMS, S(+)DMS, and combinations such as racemic mixtures of the two provide a more advantageous way of obtaining selegiline therapeutic effects in selegiline-responsive diseases or conditions. This is particularly true for diseases or conditions characterized by neoplastic cells such as, for example, cancerous cells, or cells that proliferate in an unregulated manner.

Thus, the present invention provides novel pharmaceutical compositions in which R(-)DMS, S(+)DMS, or a combination, such as a racemic mixture, of the two is employed as the active ingredient. Also provided are novel therapeutic methods involving the administration of such compositions. More specifically, the present invention provides:

(1) A pharmaceutical composition comprising an amount of R(−)DMS, S(+)DMS, or a combination of the two, such that one or more unit doses of said composition (1) A pharmaceutical composition comprising an amount of R(−)DMS, S(+)DMS, or a combination of the two, such that one or more unit doses of said composition administered on a periodic basis is effective to treat one or more neoplastic diseases or conditions in a subject to whom said unit dose or unit doses are administered. This composition may be formulated for non-oral or oral administration.

(2) A method of treating a neoplastic condition in a subject, such as a mammal, which comprises administering to said mammal R(−)DMS, S(+)DMS, or a combination of the two, in a dosage regimen effective to produce a selegiline therapeutic effect, such as a daily dose, administered in a single or multiple dosage regimen of at least about 0.0015 mg, calculated on the basis of the free secondary amine, per kg. of the mammals body weight.

(3) A transdermal delivery-system for use in treating a neoplastic condition in a mammal which comprises a layered composite of one or more layers with at least one layer including an amount of R(−)DMS, S(+)DMS, or a combination of the two sufficient to supply a daily transdermal dose of at least about 0.0015 mg of the free secondary amine, per kg of the mammal's body weight; and (4) A therapeutic package for dispensing to, or for use in dispensing to, a patient being treated for a neoplastic disease or condition. The package contains one or more unit doses, each such unit dose comprising an amount of R(−)DMS, S(+)DMS or a combination of the two, such that periodic administration is effective in treating the patient's neoplastic disease or condition. The therapeutic package also comprises a finished pharmaceutical container containing the unit doses of R(−)DMS, S(+)DMS, or combination thereof, and further containing or comprising labeling directing the use of the package in the treatment of the neoplastic disease or condition. The unit doses may be adapted for oral administration, e.g. as tablets or capsules, or may be adapted for non-oral administration.

(5) A method of dispensing R(−)DMS, S(+)DMS, or a combination of the two, to a patient being treated for a neoplastic disease or condition. The method comprises providing patients with a therapeutic package having one or more unit doses of desmethylselegiline, ent-desmethylselegiline or a mixture of the two, in an amount such that periodic administration to the patient is effective in treating their selegiline-responsive neoplastic disease or condition. The package also comprises a finished pharmaceutical container containing the desmethylselegiline, ent-desmethylselegiline, or a mixture of the two, and having labeling directing the use of the package in the treatment the selegiline-responsive neoplastic disease or condition. The unit doses in the package may be adapted for either oral or non-oral.

Preferred embodiments of the present disclosure are methods for obtaining a selegiline therapeutic effect in a patient with a neoplastic disease or condition, by administering to the patient R(−)DMS, S(+)DMS, or a mixture of R(−)DMS and S(+)DMS. Preferably the patient is a mammal, more preferably a human or a domesticated animal. The R(−)DMS, S(+)DMS, or a mixture of both enantiomers is preferably administered in a dosage regimen effective to suppress or inhibit, in whole or in part, occurrence, reoccurrence, or progression of the neoplastic disease or condition. In preferred embodiments, R(−)DMS or S(+)DMS is administered in a substantially enantiomerically pure form. In other preferred embodiments, R(−)DMS and/or S(+)DMS are administered as the free base or as an acid addition salt. Preferably the acid addition salt is hydrochloride salt. In yet another preferred embodiment, the neoplastic disease or condition treated by administering R(−)DMS, S(+)DMS, or a combination of the two, is a mammary tumor or a pituitary tumor.

In another preferred embodiment of the present disclosure, R(−)DMS, S(+)DMS, or a mixture of both enantiomers is administered at a daily dose of between about 0.02 mg/kg and about 5.0 mg/kg, more preferably at a daily dose of between about 0.6 mg/kg and about 0.8 mg/kg, calculated on the basis of the free secondary amine. In preferred embodiments of the present disclosure, the R(−)DMS, S(t) DMS, or a combination of the two is administered by an oral route of administration, or a non-oral route of administration. Non-oral routes of administration preferably include sublingual, buccal, parenteral, or transdermal administration. In a preferred embodiment, R(−)DMS, S(+)DMS, or a combination of the two is administered by a transdermal patch.

Another preferred embodiment of the present disclosure is a pharmaceutical composition that includes R(−)DMS, S(+)DMS, or a mixture of R(−)DMS and S(+)DMS, as well as a second therapeutic agent useful in the treatment of a neoplastic disease or condition. In a preferred embodiment, one or more therapeutic agents are included in the pharmaceutical composition. In another preferred embodiment, the R(−)DMS, S(+)DMS, or mixture of R(−)DMS and S(+)DMS, and the second therapeutic agent, are present in the pharmaceutical composition in an amount such that one or more unit doses of the composition are effective to suppress or inhibit, in whole or in part, progression of the neoplastic disease or condition. In other preferred embodiments, R(−)DMS and/or S(+)DMS are administered as the free base or as an acid addition salt. Preferably the acid addition salt is hydrochloride salt. In yet another preferred embodiment, the neoplastic disease or condition treated by a pharmaceutical composition with R(−)DMS, S(+)DMS, or a combination of the two, and a second therapeutic agent, is a mammary tumor or a pituitary tumor. In another preferred embodiment of the present disclosure, the second therapeutic agent is an anti-neoplastic agent or a chemotherapeutic agent. Preferably the anti-neoplastic agent is tamoxifen, cisplatin, paclitaxel, or methotrexate. In a preferred embodiment the second therapeutic agent is a radiation implant.

In other preferred embodiments, the R(−)DMS, S(+)DMS, or combination of the two enantiomers in a unit dose of the pharmaceutical composition is between about 0.02 and about 5.0 mg/kg, more preferably between about 0.6 and about 0.8 mg/kg, calculated on the basis of the free secondary amine. In another preferred embodiment, the R(−)DMS, S(+)DMS, or combination of the two enantiomers in a unit dose of the pharmaceutical composition is between about 1.0 mg and about 100.0 mg, more preferably between about 5.0 mg and about 10.0 mg. In yet another preferred embodiment, the pharmaceutical composition is for oral administration, for non-oral administration, or for transdermal administration. In a preferred embodiment the pharmaceutical composition is a transdermal patch.

Preferred embodiments of the present disclosure are also directed to methods for obtaining a selegiline therapeutic effect in a patient with a neoplastic disease or condition, by administering to the patient a pharmaceutical composition that includes R(−)DMS, S(+)DMS, or a mixture of R(−)DMS and S(+)DMS, as well as a second therapeutic agent useful in the treatment of a neoplastic disease or condition. In another preferred embodiment, one or more unit doses of the pharmaceutical composition are effective to suppress or inhibit, in whole or in part, occurrence, reoccurrence, or progression of the neoplastic disease or condition. Other preferred embodiments of the present disclosure are directed to methods for obtaining a selegiline therapeutic effect in a patient with a neoplastic disease or condition, by administering to the patient R(−)DMS, S(+)DMS, or a mixture of R(−)DMS and S(+)DMS in combination with a second therapy useful in the treatment of a neoplastic disease or condition, in a dosage regimen effective to suppress or inhibit, in whole or in part, occurrence, reoccurrence, or progression of the neoplastic disease or condition. Preferably the second therapy is chemotherapy or radiation.

BRIEF DESCRIPTION OF THE SEVERAL VIEWS OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
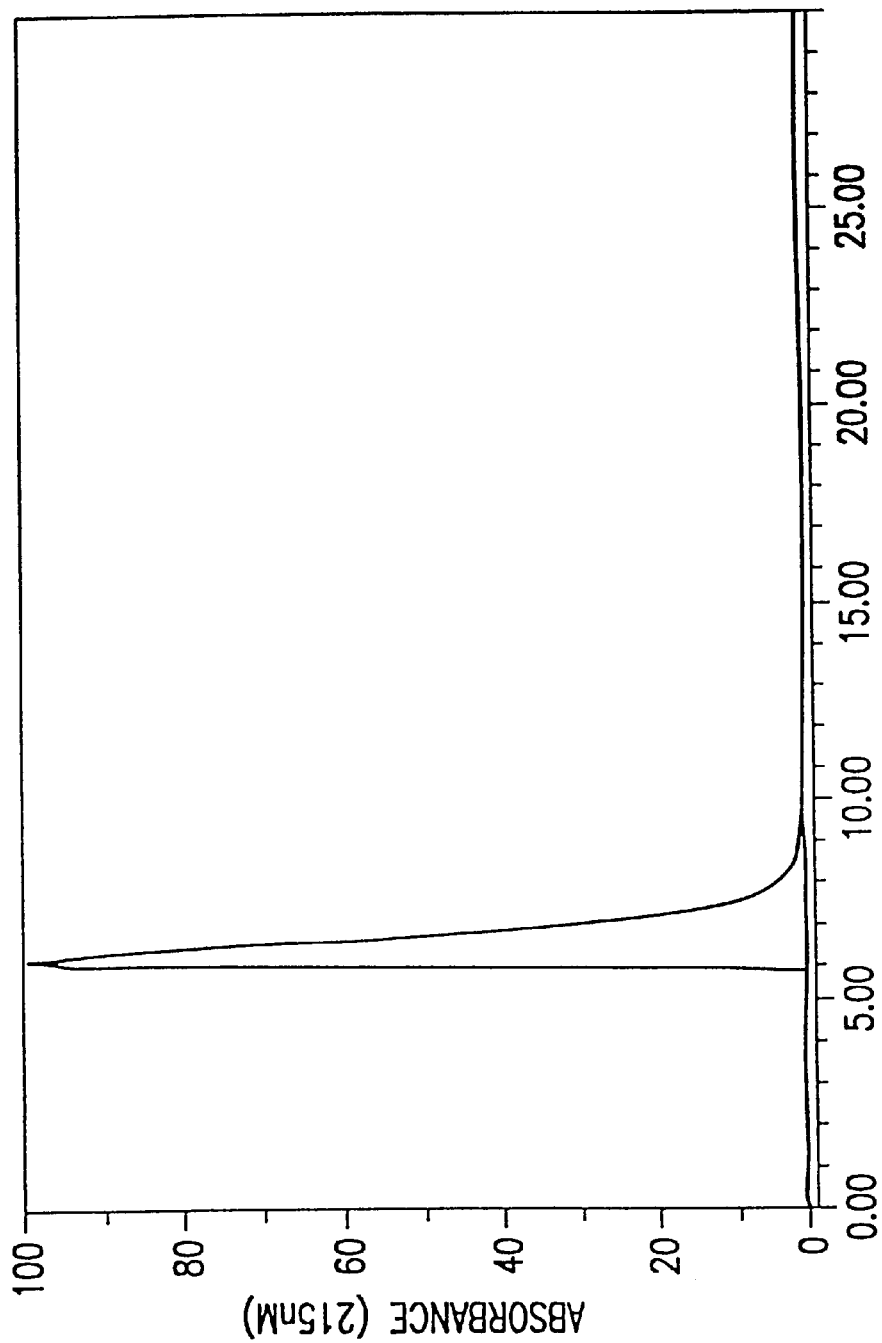
FIG. 1: HPLC Chromatogram of Purified R(−)DMS (Microsorb MV Cyano Column). The purity of a preparation of R(−)DMS was determined by HPLC on a Microsorb MV Cyano column and results are shown in FIG. 1. The column had dimensions of 4.6 mm×15 cm. and was developed at a flow rate of 1.0 ml/min using a mobile phase containing 90% 0.01M $H_3PO_4$ (pH 3.5) and 10% acetonitrile. The column was run at a temperature of 40° C. and effluent was monitored at a wavelength of 215 nm. The chromatogram shows one major peak appearing at a time of 6.08 minutes and having 99.5% of the total light-absorbing material eluted from the column. No other peak had greater than 0.24%.

As used herein the term "selegiline-responsive disease or condition" refers to any of the various diseases or conditions in mammals, including humans, for which selegiline is known as being therapeutically useful, such as, for example, the various diseases and conditions described above, e.g., Parkinson's disease, cognitive dysfunction, neuronal rescue, neoplastic diseases, and the like. Similarly, the term "selegiline therapeutic effect" refers to one or more of the salutary effects reported as being exerted by selegiline in subjects being treated for a selegiline-responsive disease or condition.

As used herein, the term "neoplastic disease or condition" refers to any type of disease or condition such as, but not limited to, any known selegiline-responsive neoplasms, any malignant or benign neoplasms, including any type of diffuse neoplasm such as leukemia, as well as malignant or benign cancers and tumors (including any carcinoma, sarcoma, or adenoma). A neoplasm is abnormal tissue that grows by cellular proliferation more rapidly than normal, and can continue to grow after the stimuli that initiated the new growth has ceased. A neoplasm may also have partial or complete lack of structural organization and functional coordination with normal tissue. Specifically contemplated neoplastic diseases or conditions are, for example, tumors such as tumors of the mammary, pituitary, thyroid, or prostate gland; tumors of the brain, liver, meninges, bone, ovary, uterus, cervix, and the like; as well as both monocytic and myelogenous leukemia.

Additional specifically contemplated neoplastic diseases or conditions include, but are not limited to, adenocarcinoma, adenoma, astrocytoma, bladder tumor, brain tumor, Burkitt lymphoma, breast carcinoma, cervical carcinoma, colon carcinoma, kidney carcinoma, liver carcinoma, lung carcinoma, ovarian carcinoma, pancreatic carcinoma, prostate carcinoma, rectal carcinoma, skin carcinoma, stomach carcinoma, testis carcinoma, thyroid carcinoma, chondrosarcoma, choriocarcinoma, fibroma, fibrosarcoma, glioblastoma, glioma, hepatoma, histiocytoma, leiomyoblastoma, leiomyosarcoma, lymphoma, liposarcoma cell, mammary tumor, medulloblastoma, myeloma, plasmacytoma, neuroblastoma, neuroglioma, osteogenic sarcoma, pancreatic tumor, pituitary tumor, retinoblastoma, rhabdomyosarcoma, sarcoma, testicular tumor, thymoma, Wilms' tumor, and the like.

As stated, the present invention encompasses the inhibition, prevention, or suppression of neoplastic diseases or conditions by use of DMS in the form of R(−)DMS, S(+)DMS, or mixtures of R(−)DMS and S(+)DMS. As used herein, the term R(−)DMS means the R(−) enantiomeric form of DMS, including as a free base, as well as any acid addition salt thereof. Likewise, the term S(+)DMS, as used herein, encompasses the S(+) enantiomeric form of DMS, including as a free base, as well as any acid addition salt thereof Such salts of either R(−)DMS or S(+)DMS include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like. Accordingly, reference herein to the administration of either or both R(−)DMS and S(+)DMS encompasses both the free base and acid addition salt forms. When either R(−)DMS or S(+)DMS is used alone in the presently disclosed compositions and methods, it is used in a substantially enantiomerically pure form. Reference to mixtures or combinations of R(−)DMS and S(+)DMS includes both racemic and non-racemic mixtures of optical isomers.

The inhibition, prevention, or suppression of neoplastic diseases or conditions will occur when either or both forms of DMS are administered to animals. Preferably, R(−)DMS and/or S(+)DMS will prevent or inhibit the occurrence or reoccurrence of a neoplastic disease or condition. The neoplastic conditions or diseases treatable include but are not limited to, those listed above as selegiline-responsive neoplastic diseases or conditions.

Because the use of R(−)DMS and/or S(+)DMS to promote healthy functioning of the immune system is also known (see related applications SN 679,330 and SN 679,328 (U.S. Pat. No. 6,033,682)), the use of these substances to suppress or inhibit neoplastic disease conditions can be used simultaneously to improve immune system functioning during periods when it may be depressed due to other cancer chemotherapeutic regimens or other medical conditions.

R(−)DMS and/or S(+)DMS may be administered either by an oral route (involving gastrointestinal absorption) or by a non-oral route (does not rely upon gastrointestinal absorption, i.e. a route that avoids absorption of R(−)DMS and/or S(+)DMS from the gastrointestinal tract). Depending upon the particular route employed, the DMS is administered in the form of the free base or as a physiologically acceptable non-toxic acid addition salt as described above. The use of salts, especially the hydrochloride, is particularly desirable when the route of administration employs aqueous solutions, as for example parenteral administration; use of delivered desmethylselegiline in the form of the free base is especially useful for transdermal administration. Although the oral route of administration will generally be most convenient, R(−)DMS, S(+)DMS, or a mixture of both may be administered by the parenteral, topical, transdermal, intraocular, buccal, sublingual, intranasal, inhalation, vaginal, rectal or other routes as well.

The optimal daily dose of R(−)DMS, S(+)DMS, or of a combination thereof, such as a racemic mixture of R(−)DMS and S(+)DMS, useful for the purposes of the present invention is determined by methods known in the art, e.g., based on the severity of the disease or condition being treated, the condition of the subject to whom treatment is being given, the desired degree of therapeutic response, and the concomitant therapies being administered to the patient or animal. Ordinarily, however, the attending physician or veterinarian will administer an initial dose of at least about 0.015 mg/kg, calculated on the basis of the free secondary amine, with progressively higher doses being employed depending upon the route of administration and the subsequent response to the therapy. Typically the daily dose will be from about 0.2 mg/kg or 0.05 mg/kg to about 0.10 mg/kg or about 0.15 mg/kg to about 0.175 mg/kg or about 0.20 mg/kg or about 0.5 mg/kg and may extend to about 1.0 mg/kg or even 1.5, 2.0, 3.0 or 5.0 mg/kg of the patient's body weight depending on the route of administration. Preferred daily doses will be in the range of about 0.10 mg/kg to about 1.0 mg/kg. More preferred daily doses will be in the range of about 0.4 mg/kg to about 0.9 mg/kg. Even more preferred daily doses will be in the range of about 0.6 mg/kg to about 0.8 mg/kg. Again, all such doses should be calculated on the basis of the free secondary amine. These guidelines further require that the actual dose be carefully titrated by the attending physician or veterinarian depending on the age, weight, clinical condition, and observed response of the individual patient or animal.

Unit doses of pharmaceutical compositions that include R(−)DMS, S(+)DMS, or a mixture of R(−)DMS and S(+)DMS, are preferably between about 1.0 mg and about 100.0 mg, preferably between about 5.0 mg and about 80 mg, more preferably between about 10.0 mg and about 50.0 mg. Typically the unit dose of the pharmaceutical composition will be from about 0.02 mg or 0.05 mg to about 0.10 mg or about 0.15 mg to about 0.175 mg or about 0.20 mg or about 0.5 mg and may extend to about 1.0 mg or even to about 1.5 mg, 2.0 mg, 3.0 mg, 5.0 mg, 10 mg, 20 mg, 30 mg, 50 mg, 100 mg, or 250 mg. When ranges for daily doses, unit doses, dosages, concentrations, or the like are given in the present disclosure, any numerical values recited herein include all values from the lower value to the upper value in increments of one unit. As an example, if it is stated that the amount of a component or a value of a process variable such as, for example, daily dose, unit dose, and the like is, for example, from 1 to 100, preferably from 5 to 80, more preferably from 10 to 50, it is intended that values such as 15 to 85, 22 to 68, 43 to 51, 30 to 32, etc. are expressly enumerated in this disclosure. For values that are less than one, one unit is considered to be 0.0001, 0.001, 0.01, or 0.1 as appropriate. For values that are less than ten, one unit is considered to be 0.1, 0.25, 0.5, or 0.75 as appropriate. These are only examples of what is specifically intended and all possible combinations of numerical values between the lowest value and the highest value enumerated are to be considered to be expressly stated in this application in a similar manner.

The daily dose can be administered in a single or multiple dosage regimen. Either oral or non-oral dosage forms may be used and may permit, for example, a burst of the active ingredient from a single dosage unit, such as an oral composition, or a continuous release of relatively small amounts of the active ingredient from a single dosage unit, such as a transdermal patch, over the course of one or more days. Alternatively, intravenous or inhalation routes may be preferred.

Pharmaceutical compositions containing one or both R(−)DMS or S(+)DMS can be prepared according to conventional techniques. For example, preparations for parenteral routes of administration, e.g., intramuscular, intravenous and intraarterial routes, can employ sterile isotonic saline solutions. Sterile buffered solutions can also be employed for intraocular administration.

Transdermal dosage unit forms of R(−)DMS and/or S(+)DMS can be prepared utilizing a variety of previously described techniques (see e.g., U.S. Pat. Nos. 4,861,800; 4,868,218; 5,128,145; 5,190,763; and 5,242,950; and EP-A 404807, EP-A 509761, and EP-A 593807). For example, a monolithic patch structure can be utilized in which desmethylselegiline is directly incorporated into the adhesive and this mixture is cast onto a backing sheet. Alternatively R(−)DMS and/or S(+)DMS, can be incorporated as an acid addition salt into a multilayer patch which effects a conversion of the salt to the free base, as described for example in EP-A 593807.

One or both R(−)DMS or S(+)DMS can also be administered by a device employing a lyotropic liquid crystalline composition in which, for example, 5 to 15% of desmethylselegiline is combined with a mixture of liquid and solid polyethylene glycols, a polymer, and a nonionic surfactant, optionally with the addition of propylene glycol and an emulsifying agent. For further details on the preparation of such transdermal preparations, reference can be made to EP-A 5509761.

Subjects treatable by the present preparations and methods include both human and non-human subjects. Accordingly, the compositions and methods above provide especially useful therapies for mammals, including humans, and in domesticated mammals. Thus, the present methods and compositions are used in treating neoplastic diseases or conditions in human, primate, canine, feline, bovine, equine, ovine, murine, caprine, and porcine species, and the like.

Successful use of the compositions and methods above requires employment of an effective amount of R(−)DMS, S(+)DMS, or mixtures of the two. As described above and notwithstanding its demonstrably inferior inhibitory properties with respect to MAO-B inhibition, R(−)DMS and its enantiomer appear to be at least as effective as selegiline in treating certain selegiline-responsive conditions, e.g., neoplastic diseases or conditions.

The present invention further encompasses the additional discovery that R(−)DMS, S(+)DMS, or combinations of the two (which are conveniently prepared by methods known in the art, as described in Example 1) may also be formulated with additional therapeutic agents, including but not limited to anti-neoplastic agents, chemotherapeutic agents, or even cocktails, to effectively treat a neoplastic disease or condition. Additional therapeutic agents useful in the treatment of neoplastic diseases or conditions include, but are not limited to, tamoxifen, taxotere, doxorubicin, cisplatin, cyclophosphamide, paclitaxel, methotrexate, mechlorethamine, aldesleukin, altretamine, amsacrine, azacitidine, ifosfamide, melphalan, chlorambucil, hexamethylmelamine, thiotepa, triethylenethiophosphoramide, busulfan, carmustine, lomustine, semustine, streptozocin, dacarbazine, fluorouacil, floxuridine, fludarabine, goserelin, cytarabine, levamisole, mercaptopurine, thioguanine, pentostatin, pipobroman, vinblastine, vincristine, vindesine, etoposide, teniposide, dactinomycin, daunorubicin, estramustine, filgrastim, bleomycin, plicamycin, uracil mustard, mitomycin, L-asparaginase, interferon-alpha, carboplatin, mitoxantrone, hydroxyurea, procarbazine, mitotane, aminoglutethimide, prednisone, hydroxyprogesterone caproate, medroxyprogesterone acetate, megastrol acetate, diethylstilbestrol, ethinyl estradiol, testosterone propionate, fluoxymesterone, flutamide, and leuprolide, an interferon, a tumor necrosis factor, a radiation implant such as a pellet or seed, or variants thereof The present invention further encompasses methods for obtaining a selegiline therapeutic effect in a patient with a neoplastic disease or condition by administering to the patient a pharmaceutical composition that includes R(−)DMS, S(+)DMS, or combinations of the two (which are conveniently prepared by methods known in the art, as described in Example 1) and one or more additional therapeutic agents, including but not limited to anti-neoplastic agents, chemotherapeutic agents, or even cocktails, to effectively treat a neoplastic disease or condition. Such pharmaceutical composition may also be used to inhibit, prevent, or suppress a neoplastic disease or condition. The therapeutic agents used in combination with R(−)DMS, S(+)DMS, or a mixture of the two to treat a neoplastic disease or condition can also be presented to the patient in a separate formulation than the R(−)DMS, S(+)DMS, or racemic mixture. Thus, separate administration of a therapeutic agent or even an administration which is spaced in time is contemplated by the present disclosure, particularly when the therapeutic agent and the DMS enantiomer or DMS enantiomers have a synergistic therapeutic action.

Additionally, the present invention contemplates methods for obtaining a selegiline therapeutic effect in a patient with a neoplastic disease or condition by administering to the patient a pharmaceutical composition that includes R(−)DMS, S(+)DMS, or combinations of the two (which are conveniently prepared by methods known in the art, as described in Example 1) in combination with one or more additional treatments for neoplastic diseases or conditions, including but not limited to surgery, chemotherapy, radiation therapy, pharmacotherapy, gene therapy, and immunotherapy treatments. Radiation therapy includes but is not limited to ionizing radiation; gamma radiation from radioactive isotopes such as cobalt-60, radium, radon, iridium, or electrically generated roentgen rays; radiation by external beam, implant, pellet, or seed; or variants thereof. R(−)DMS, S(+)DMS, or combinations of the two may be administered to a patient before, during, and/or after other available treatments for neoplastic diseases or conditions. Additionally, separate administration of R(−)DMS, S(+)DMS, or a racemic mixture from the other treatments, or even an administration which is spaced in time, is contemplated by the present disclosure The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The surprising utility of R(-)DMS and S(+)DMS in treating neoplastic diseases or conditions is attributable in part to their ability to inhibit release of prolactin. In this regard, both DMS enantiomers produce a selegiline-like anti-neoplastic effect, and in certain applications may be substantially more potent. The following working examples are illustrative only, and are not intended to limit the scope of the invention.

EXAMPLE 1

Preparation of R(-)DMS and S(+)DMS

A. R(-)DMS

R(-)DMS is prepared by methods known in the art. For example, desmethylselegiline is a known chemical intermediate for the preparation of selegiline as described in U.S. Pat. No. 4,925,878. Desmethylselegiline can be prepared by treating a solution of R(-)-2-aminophenylpropane (levoamphetamine):

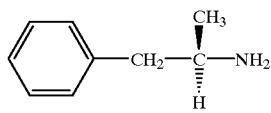

in an inert organic solvent such as toluene with an equimolar amount of a reactive propargyl halide such as propargyl bromide, Br—$CH_2$—C≡—CH, at slightly elevated temperatures (70°–90° C.). Optionally the reaction can be conducted in the presence of an acid acceptor such as potassium carbonate. The reaction mixture is then extracted with aqueous acid, for example 5% hydrochloric acid, and the extracts are rendered alkaline. The nonaqueous layer which forms is separated, for example, by extraction with benzene, dried, and distilled under reduced pressure.

Alternatively the propargylation can be conducted in a two-phase system of a water—immiscible solvent and aqueous alkali, utilizing a salt of R(+)-2-aminophenylpropane with a weak acid such as the tartrate, analogously to the preparation of selegiline as described in U.S. Pat. No. 4,564,706.

B. S(+)DMS

S(+)DMS is conveniently prepared from the enantiomeric S(+)-2-aminophenylpropane (dextroamphetamine), i.e.,

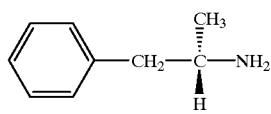

following the procedures set forth above for desmethylselegiline.

C. Mixtures of Enantiomers

Mixtures of the R(-) and S(+) enantiomeric forms of desmethylselegiline, including racemic desmethylselegiline, are conveniently prepared from enantiomeric mixtures, including racemic mixtures of the above aminophenylpropane starting material.

D. Conversion Into Acid Addition Salts

N-(prop-2-ynyl)-2-aminophenylpropane in either optically active or racemic form can be converted to a physiologically acceptable non-toxic acid addition salt by conventional techniques such as treatment with a mineral acid. For example, hydrogen chloride in isopropanol is employed in the preparation of desmethylselegiline hydrochloride. Either the free base or salt can be further purified, again by conventional techniques such as recrystallization or chromatography.

EXAMPLE 2

Characteristics of Substantially Pure R(-)DMS

Figure 2:
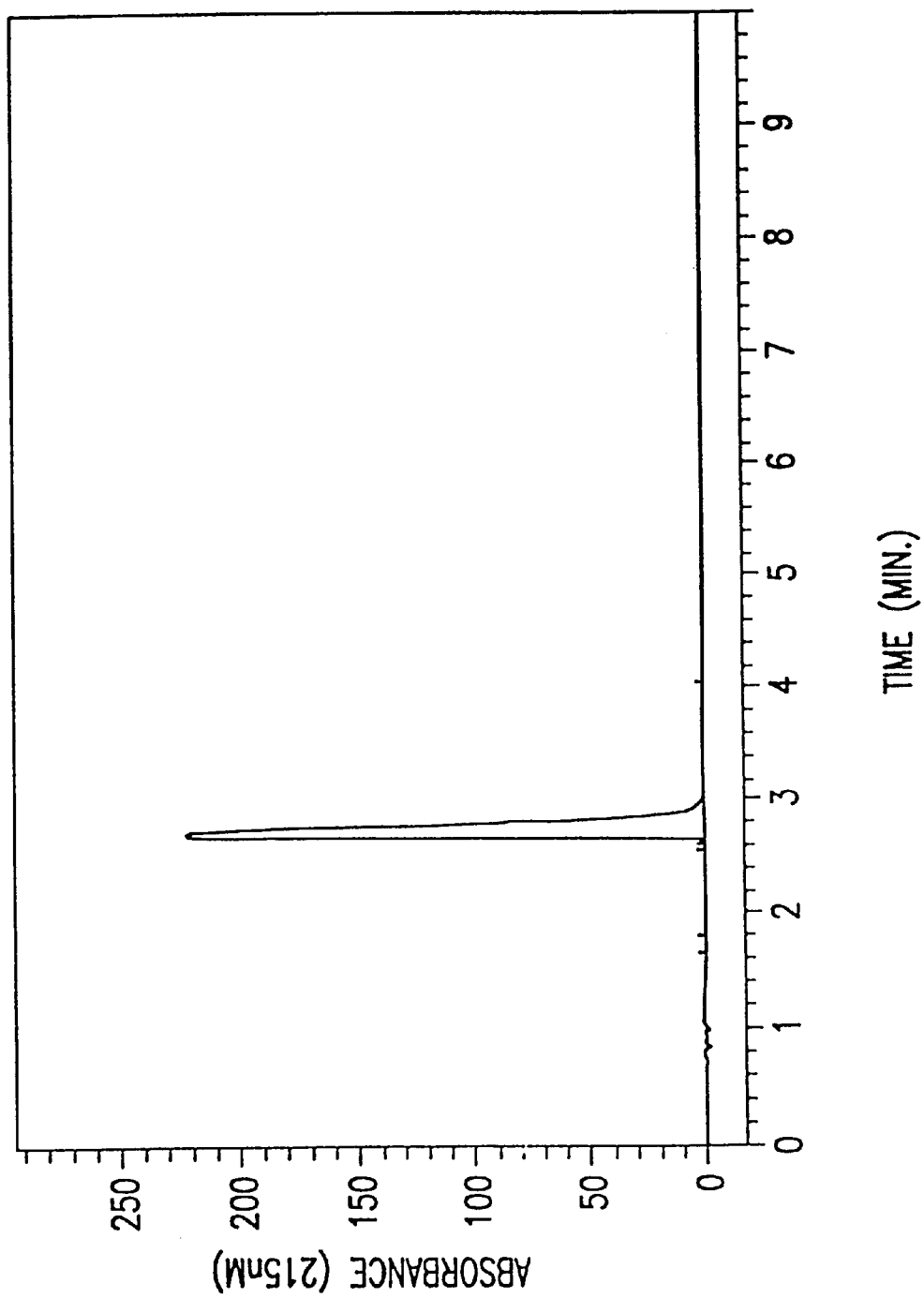
FIG. 2: HPLC Elution Profile of R(−)DMS (Zorbax Mac-Mod C 18 Column). The same preparation that was analyzed in the experiments discussed in FIG. 1 was also analyzed for purity by HPLC on a Zorbax Mac-Mod SB-C18 column (4.6 mm×75 mm). Effluent was monitored at 215 nm and results can be seen in FIG. 2. Greater than 99.6% of the light-absorbing material appeared in the single large peak eluting at a time of between 2 and 3 minutes.
Figure 3:
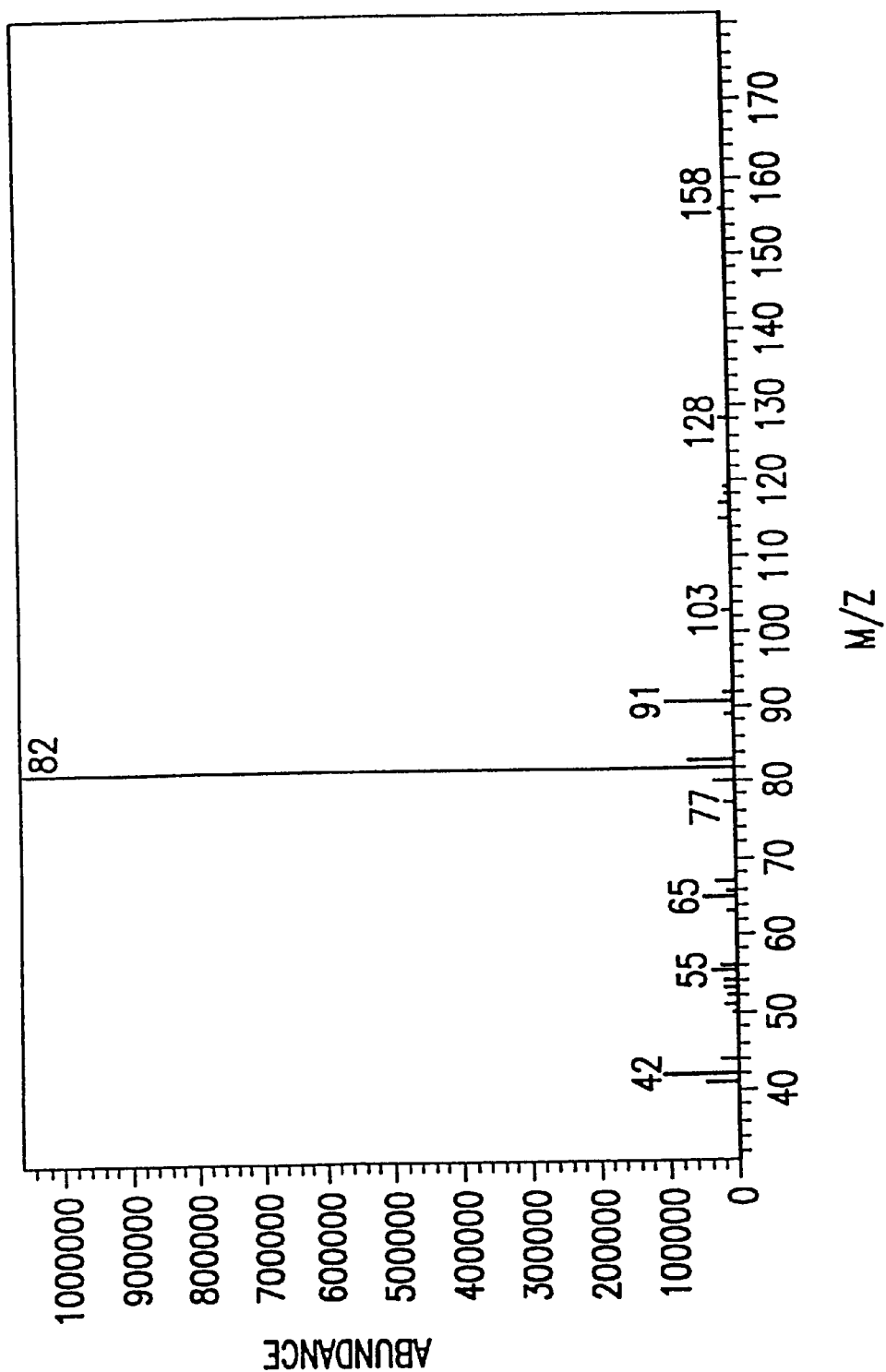
FIG. 3: Mass Spectrum of R(−)DMS. A mass spectrum was obtained for purified R(−)DMS and results are shown in FIG. 3. The spectrum is consistent with a molecule having a molecular weight of 209.72 amu and a molecular formula of $C_{12}H_{15}N$—HCl.
Figure 4:
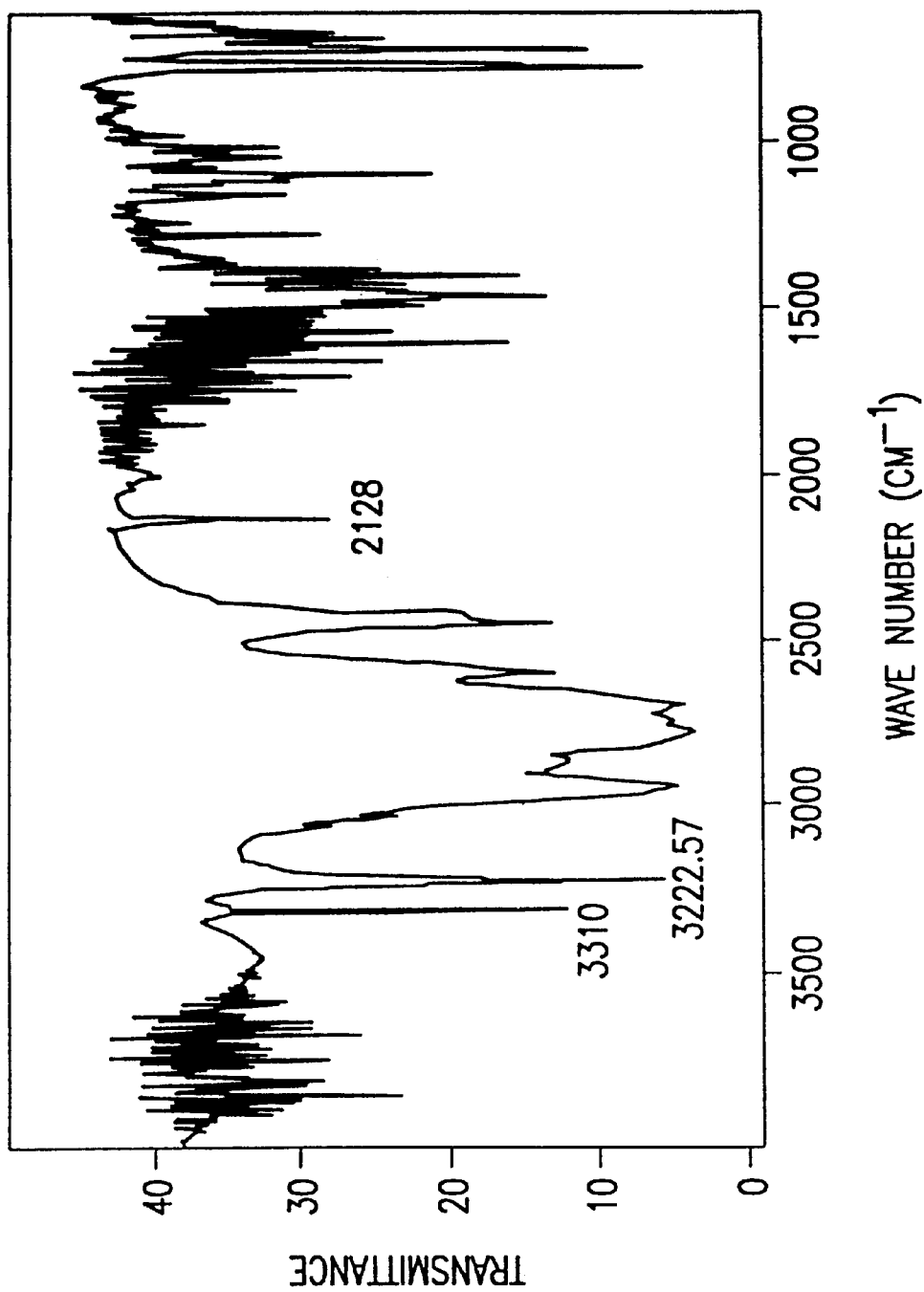
FIG. 4: Infrared Spectrum. (KBr) of Purified R(−)DMS. Infrared spectroscopy was performed on a preparation of R(−)DMS and results are shown in FIG. 4. The solvent used was $CDCl_3$.
Figure 5:
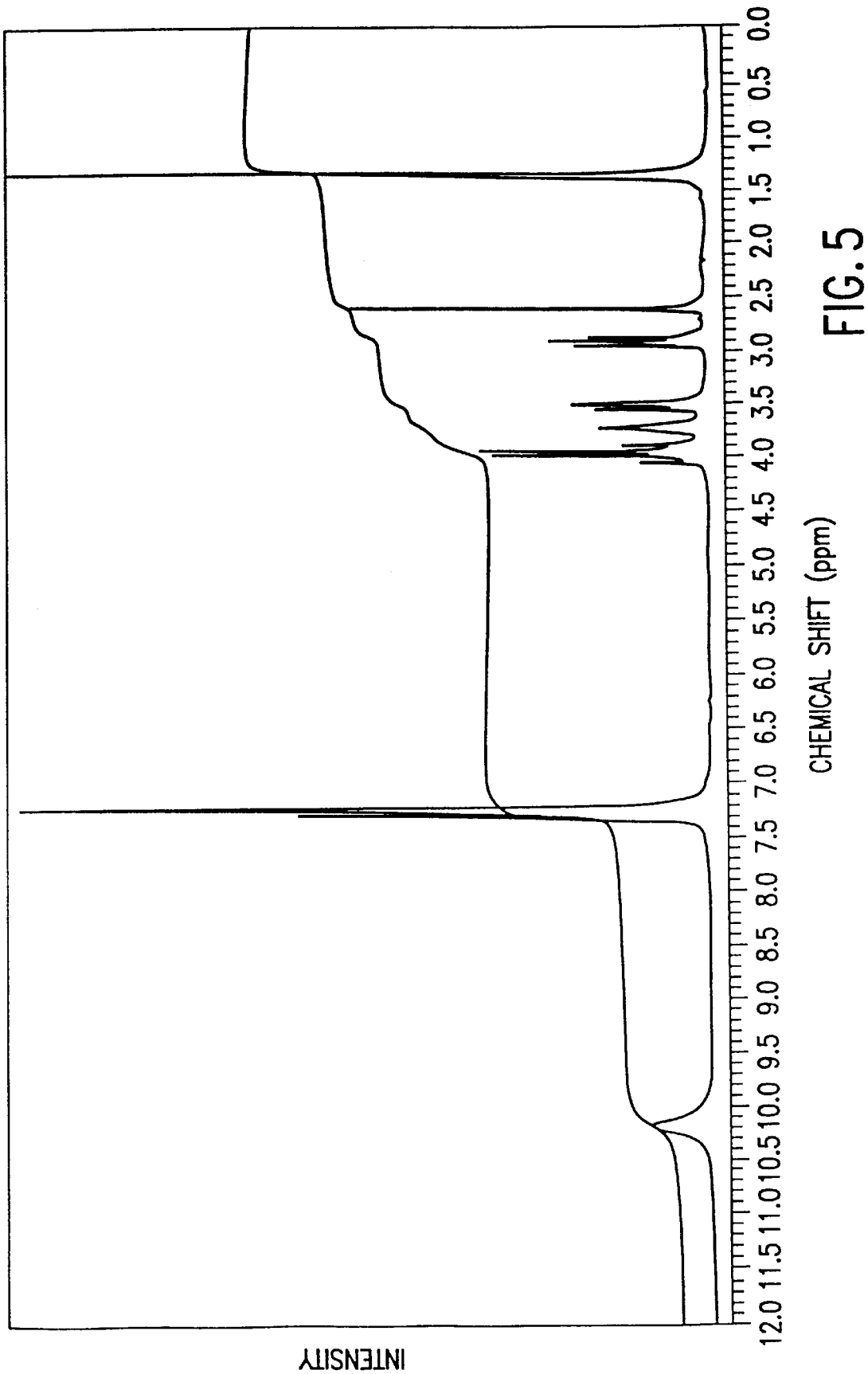
FIG. 5: NMR Spectrum of Purified R(−)DMS. A preparation of purified R(−)DMS was dissolved in $CDCl_3$ and $^1H$ NMR spectroscopy was performed at 300 nm. Results are shown in FIG. 5.

A preparation of substantially pure R(-)DMS has the appearance of a white crystalline solid with a melting point of 162–163C and an optical rotation of $[\alpha]_D^{23c}=-15.2+/-2.0$ when measured at a concentration of 1.0 M using water as solvent. R(-)DMS appeared to be 99.5% pure when analyzed by HPLC on a Microsorb MV Cyano column (see chromatogram in FIG. 1) and 99.6% pure when analyzed by HPLC on a Zorbax Mac-Mod SB-C 18 column, (see chromatogram in FIG. 2). No single impurity is present at a concentration greater than or equal to 0.5%. Heavy metals are present at a concentration of less than 10 ppm and amphetamine hydrochloride at a concentration of less than 0.03%. The last solvents used for dissolving the preparation, ethyl acetate and ethanol are both present at a concentration of less than 0.1%. A mass spectrum performed on the preparation (see FIG. 3) is consistent with a compound having a molecular weight of 209.72 amu and a formula of $C_{12}H_{15}NHCl$. Infrared and NMR spectra are shown in FIGS. 4 and 5 respectively. These are also consistent with the known structure of R-(-)-DMS.

EXAMPLE 3

Characteristics of Substantially Pure S(+)DMS

Figure 6:
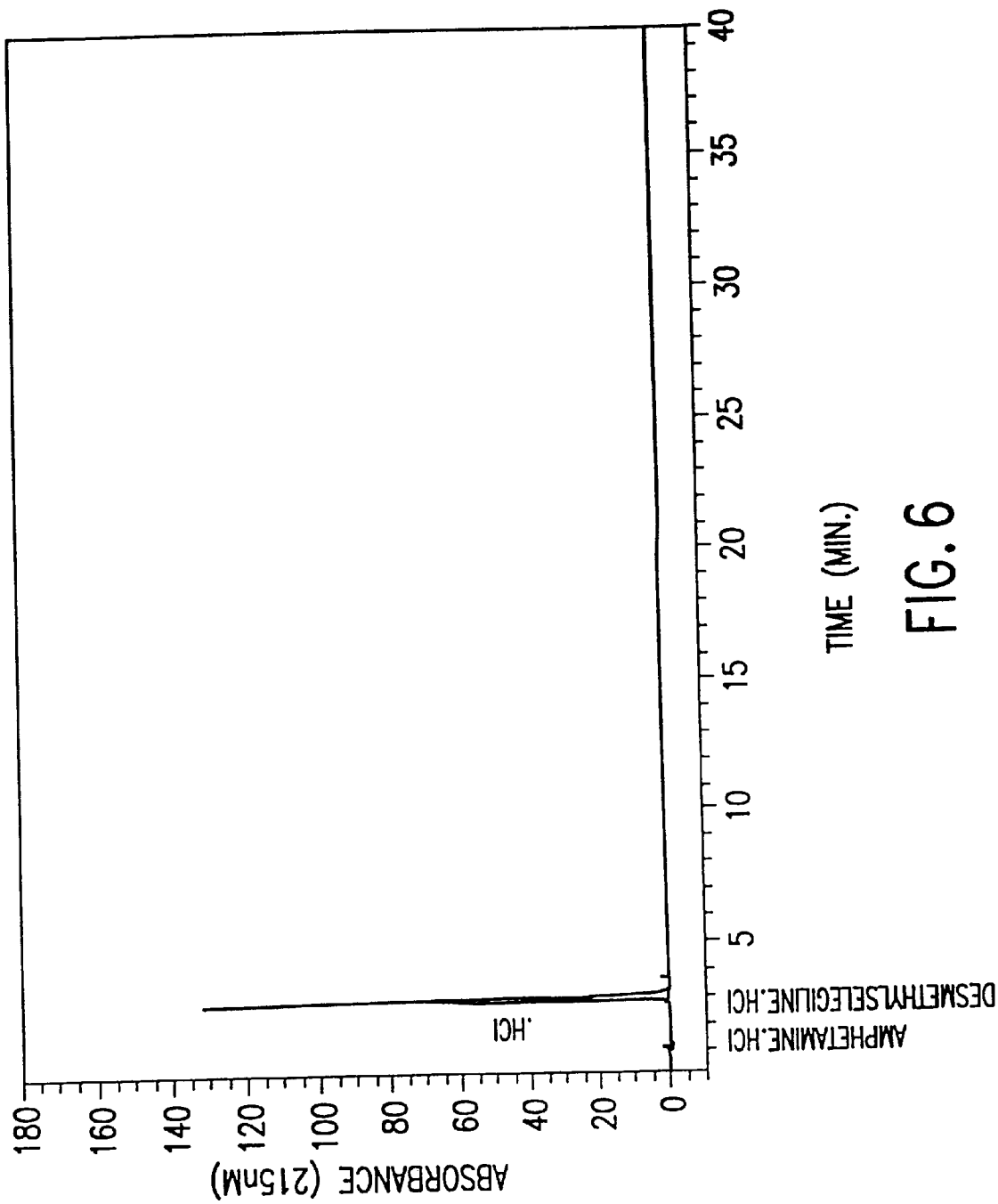
FIG. 6: HPLC Chromatogram of S(+)DMS. The purity of a preparation of S(+)DMS was examined by reverse phase HPLC on a 4.6 min×75 min Zorbax Mac-Mod SB-C18 column. The elution profile, monitored at 215 nm, is shown in FIG. 6. One major peak appears in the profile at a time of about 3 minutes and contains greater than 99% of the total light-absorbing material that eluted from the column.
Figure 7:
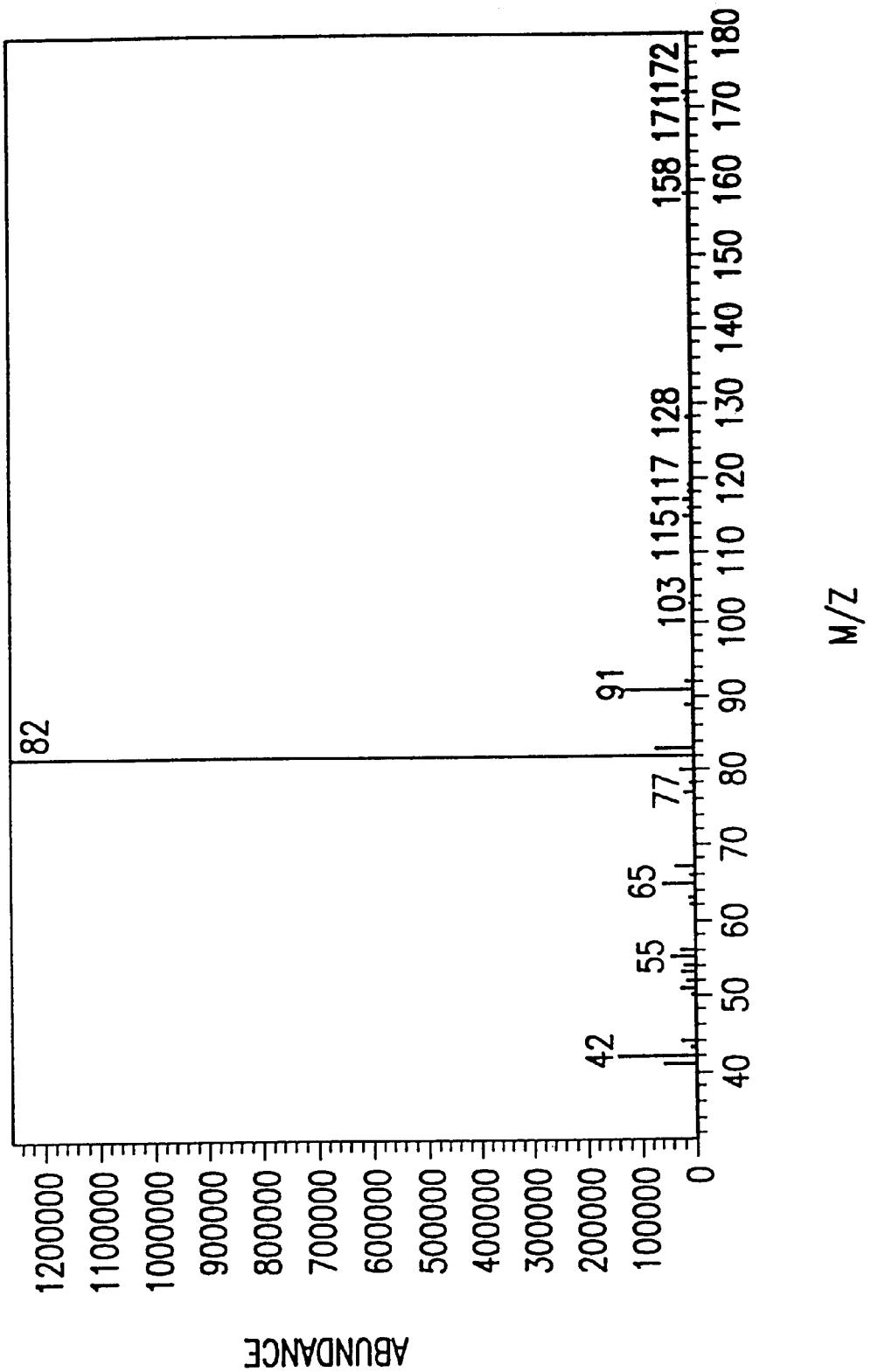
FIG. 7: Mass Spectrum of Purified S(+)DMS. Mass spectroscopy was performed on the same preparation examined in FIG. 6. The spectrum is shown in FIG. 7 and is consistent with the structure of S(+)DMS.
Figure 8:
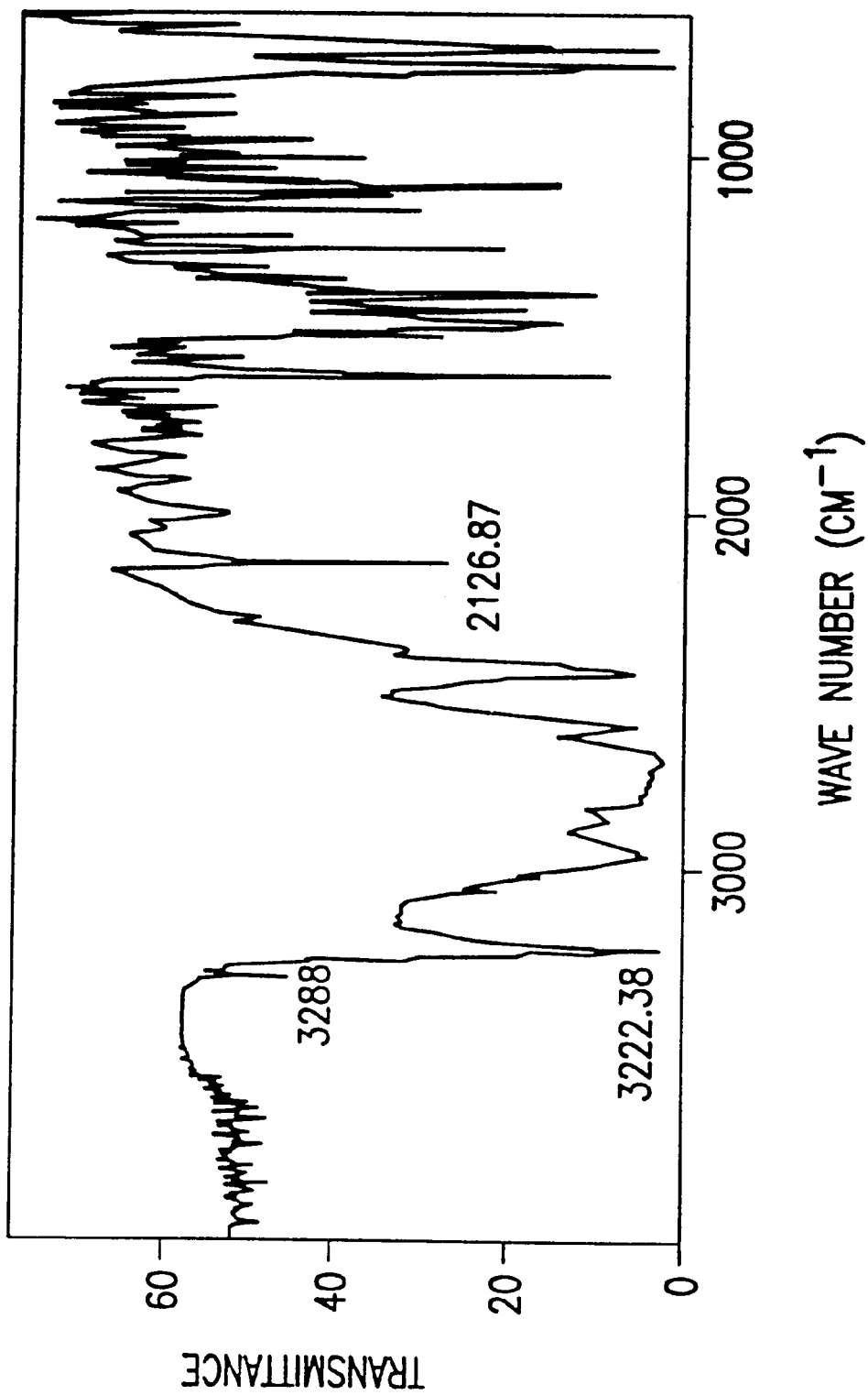
FIG. 8: Infrared Spectrum (KBr) of Purified S(+)DMS. The preparation of S(+)DMS discussed in connection with FIGS. 6 and 7 was examined by infrared spectroscopy and results are shown in FIG. 8.

A preparation of substantially pure S(+)DMS has the appearance of a white powder with a melting point of approximately 160.04° C. and a specific rotation of +15.1 degrees when measured at 22° C. in water, at a concentration of 1.0 M. When examined by reverse phase HPLC on a Zorbax Mac-Mod SB-C18 column the preparation appears to be about 99.9% pure (FIG. 6). Amphetamine hydrochloride is present at a concentration of less than 0.13% (w/w). A mass spectrum is performed on the preparation and is consistent with a compound having a molecular weight of 209.72 and a molecular formula of $C_{12}H_{15}NHCl$(see FIG. 7). Infrared spectroscopy is performed and also provides results consistent with the structure of S(+)DMS (see FIG. 8).

EXAMPLE 4

Desmethylselegiline and Ent-Desmethylselegiline as Inhibitors of Dopamine Accumulation (Uptake)

The biological actions of the brain neurotransmitter dopamine are terminated at the synapse by a high-affinity, sodium and energy-dependent transport system (neuronal accumulation or uptake, formerly referred to as "re-uptake") present within the limiting membrane of the presynaptic dopamine-containing nerve terminal. Inhibition of this transport mechanism would extend the actions of dopamine at the synapse and therefore enhance dopamine synaptic transmission.

A. Method of Testing

The R(-) and S(+) enantiomers of desmethylselegiline (DMS) were tested for their ability to inhibit the dopamine uptake system and compared to selegiline. Inhibitory activity in this assay is indicative of agents of value in the treatment of diseases which require enhanced synaptic dopamine activity. Presently this would include Parkinson's disease, Alzheimer's disease and attention deficit hyperactivity disorder (ADHD).

The assay system used was essentially that described by Fang et al., (*Neuro-pharmacology* 33:763–768 (1994)). An in vitro nerve-terminal preparation (symptosome-preparation) was obtained from fresh rat neostriatal brain tissue. Transport by dopamine nerve-terminals was estimated by measuring the uptake of tritiated dopamine.

B. Results

As seen in the data presented in Table 2, selegiline, R(−)DMS and S(+)DMS each inhibited dopamine uptake by dopamine-containing nerve terminals. Selegiline and R(−)DMS were approximately equipotent. In contrast, S(+)DMS was 4–5 times more potent than either selegiline or R(−)DMS.

TABLE 2

$^3$H-Dopamine Uptake By Rat Neostriatal Brain Tissue

| Agent | Concentration | % Reduction 0 ± SEM |
|---|---|---|
| Dopamine | 1 μM | 52.0 ± 4.9 |
|  | 10 μM | 80.9 ± 0.4 |
| Selegiline | 100 Nm | 7.0 ± 3.6 |
|  | 1 μM | 13.9 ± 4.7 |
|  | 10 μM | 16.3 ± 3.8 |
|  | 100 μM | 59.8 ± 1.0 |
| R(−)DMS | 100 nM | 11.5 ± 1.0 |
|  | 1 μM | 10.7 ± 2.8 |
|  | 10 μM | 20.1 ± 3.1 |
|  | 100 μM | 51.3 ± 2.6 |
| S(+)DMS | 100 nM | 15.3 ± 7.7 |
|  | 1 μM | 24.1 ± 11.7 |
|  | 10 μM | 47.0 ± 3.1 |
|  | 100 μM | 76.9 ± 1.8 |

Figure 9:
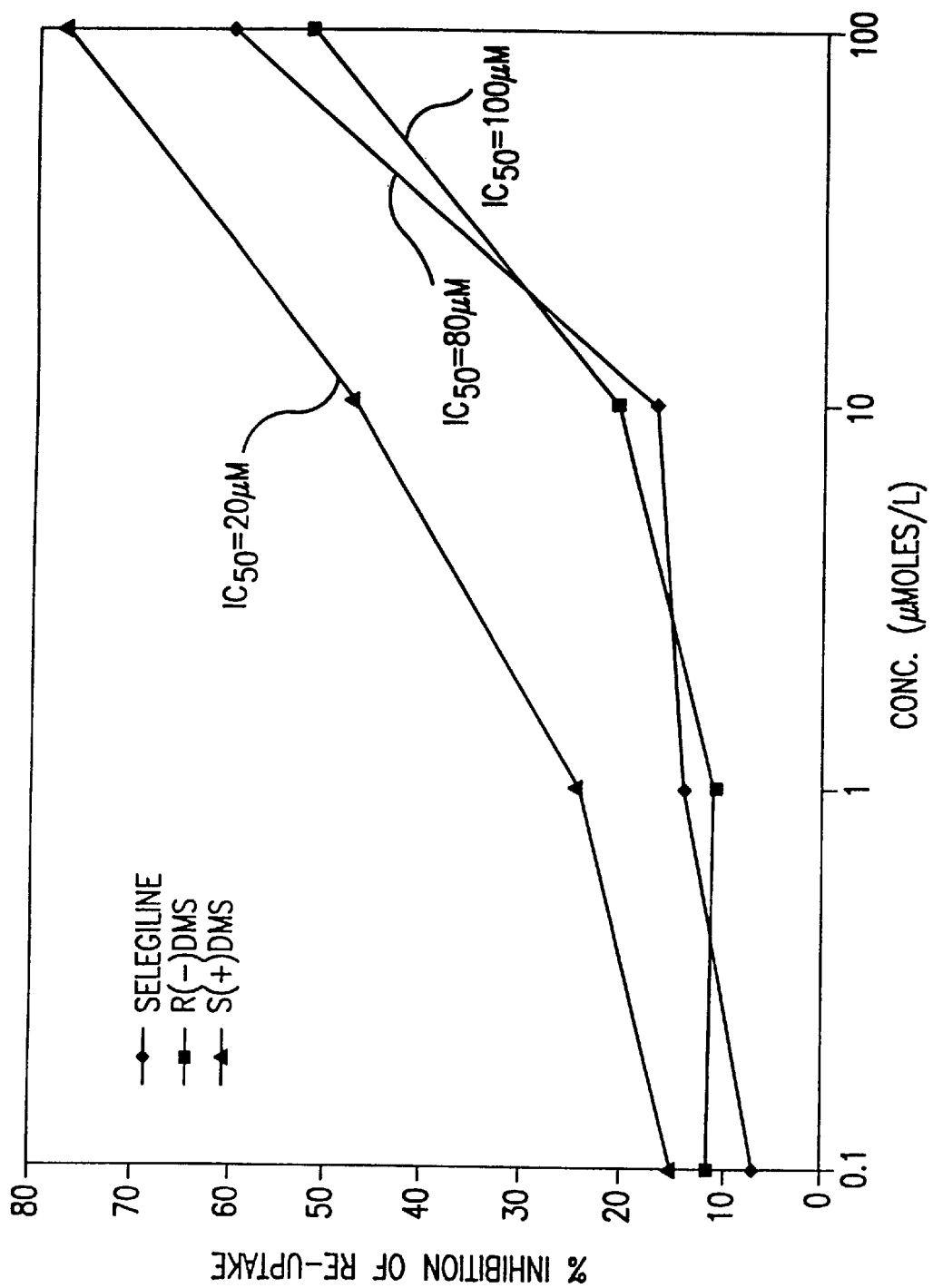
FIG. 9: Inhibition of Neuronal Dopamine Accumulation (Uptake) by Deprenyl and the Two Enantiomers of Desmethylselegiline. An in vitro nerve terminal preparation (synaptosome preparation) was prepared using fresh rat neostriatal tissue. This was examined for its ability to take up tritiated dopamine in buffer alone or in buffer supplemented with various concentrations of selegiline, R(−) desmethylselegiline or S(+) desmethylselegiline (formerly referred to as "re-uptake" assays). Uptake in the presence of each MAO inhibitor, expressed as a percent inhibition vs. log concentration of inhibitor is shown in FIG. 9. As indicated, the plot was used to determine the $IC_{50}$ for each test agent.

Relative potency can be expressed in terms of the concentration required to inhibit dopamine uptake by 50% ($IC_{50}$). The $IC_{50}$ values were determined graphically (see FIG. 9) and are shown below in Table 3.

TABLE 3

Concentrations Needed to Inhibit Dopamine Uptake by 50%

| Agent | $IC_{50}$ | Relative Potency |
|---|---|---|
| Selegiline | ≈80 μM | 1 |
| R(−)DMS | ≈100 μM | 0.8 |
| S(+)DMS | ≈20 μM | 4 |

Figure 10:
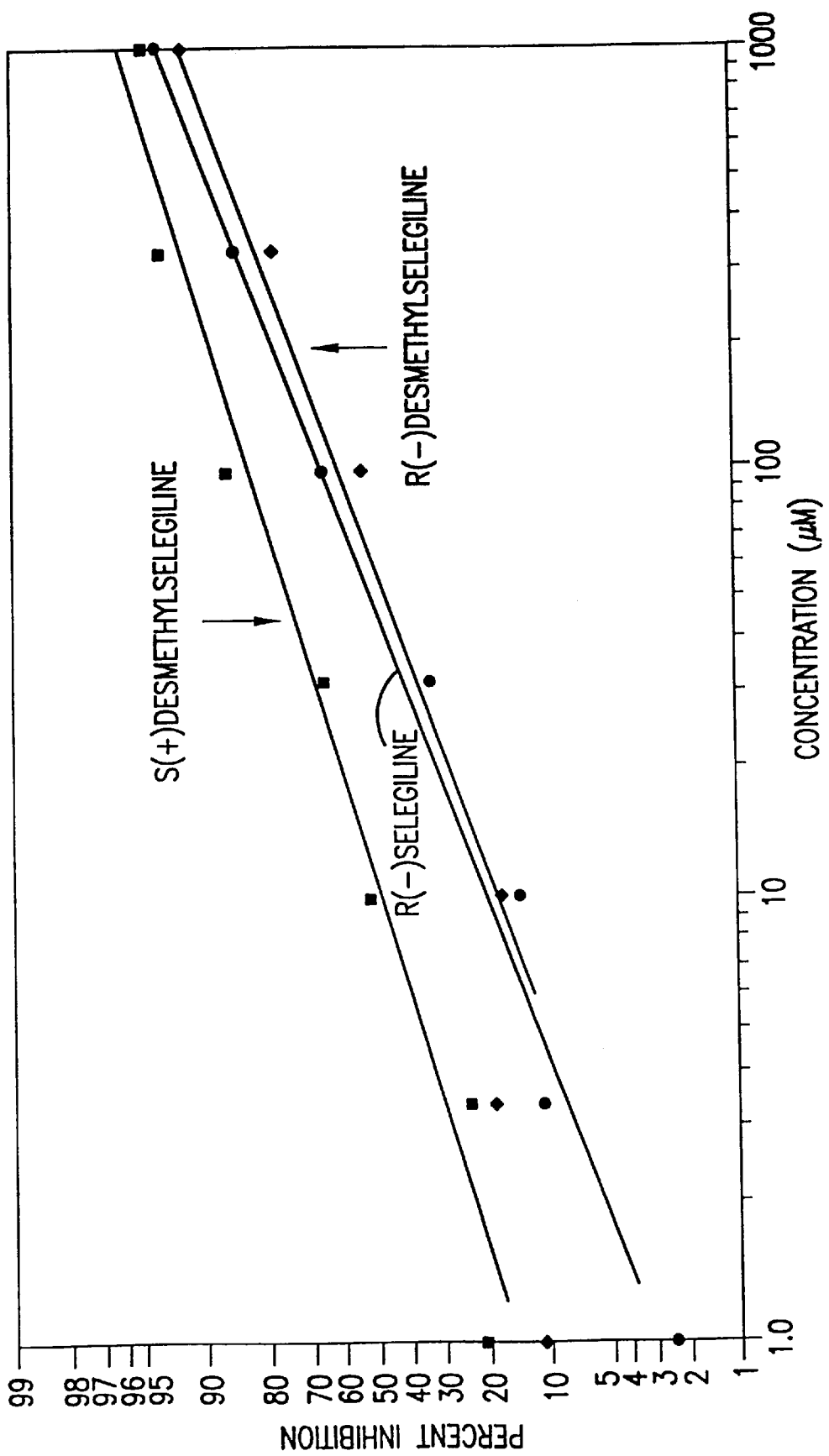
FIG. 10: Determination of $IC_{50}$ Values for Inhibition of Dopamine Accumulation (Uptake). The experiment of FIG. 9 was repeated in a concentration range designed to more accurately provide an $IC_{50}$ value and results are shown in FIG. 10. Using the log C vs. probit graphs, as shown in the figure, the $IC_{50}$ for S(+)DMS was determined to be about 11 μM; for selegiline, about 46 μM; and for R(−)DMS about 54 μM.

The experiment described above was repeated in a concentration range designed to more accurately describe $IC_{50}$ values and results are shown in FIG. 10. $ID_{50}$ values determined based upon the graph are shown in Table 4.

TABLE 4

Concentrations Needed to Inhibit Dopamine Uptake by 50%

| Compound | $IC_{50}$ | Potency Relative to Selegiline |
|---|---|---|
| S(+)DMS | 11 μM | 4.2 |
| selegiline | 46 μM | 1 |
| R(−)DMS | 54 μM | 1.2 |

C. Conclusions

The results demonstrate that, at the appropriate concentration, selegiline and each of the enantiomers of DMS inhibit transport of released dopamine at the neuronal synapse and enhance the relative activity of this neurotransmitter at the synapse. In this regard, S(+)DMS is more potent than selegiline which, in turn, is more potent than R(−)DMS. Of the agents tested, S(+)DMS is the most preferred with regard to the treatment of hypodopaminergic conditions such as ADHD.

EXAMPLE 5

Actions of the R(−) and S(+) enantiomers of Desmethylselegiline (DMS) on Human Platelet MAO-B and Guinea Pig Brain MAO-B and MAO-A Activity Human platelet MAO is comprised exclusively of the type-B isoform of the enzyme. In the present study, the in vitro and in vivo inhibition of this enzyme by the two enantiomers of DMS was determined and compared with inhibition due to selegiline. The present study also examined the two enantiomers of DMS for inhibitory activity with respect to the MAO-A and MAO-B in guinea pig hippocampal tissue. Guinea pig brain tissue is an excellent animal model for studying brain dopamine metabolism, the enzyme kinetics of the multiple forms of MAO and the inhibitory properties of novel agents that interact with these enzymes. The multiple forms of MAO in this animal species show similar kinetic properties to those found in human brain tissue. Finally, the test agents were administered to guinea pigs and the extent to which they might act as inhibitors of brain MAO in vivo was assessed.

A. Method of Testing

In vitro: The test system utilized the in vitro conversion of specific substrates of MAO-A ($^{14}$C-serotonin) in guinea pig hippocampal homogenates or MAO-B ($^{14}$C-phenylethylamine) by human platelets and guinea pig hippocampal homogenates. The rate of conversion of each substrate was measured in the presence of S(+)DMS, R(−)DMS or selegiline and compared to the isozyme activity in the absence of these agents. A percent inhibition was calculated from these values. Potency was evaluated by comparing the concentration of each agent which caused a 50% inhibition($IC_{50}$ value).

In vivo: R(−)DMS, S(+)DMS or selegiline was administered in vivo subcutaneously (sc), once a day for 5 days prior to sacrifice. Hippocampal homogenates containing enzyme were prepared, and assays in vitro for MAO-A and MAO-B activity. These experiments were performed to demonstrate that the DMS enantiomers were capable of entering brain tissue and inhibiting MAO activity.

B. Results

MAO-B Inhibitory Activity In Vitro

Results for MAO-B inhibition are shown in Tables 5 and 6. $IC_{50}$ values for MAO-B inhibition and potency as compared to selegiline is shown in Table 7.

TABLE 5

MAO-B Inhibition in Human Platelets Concentration

| Agent | Concentration | % Inhibition 0 ± SEM |
|---|---|---|
| Selegiline | 0.3 nM | 8.3 ± 3.4 |
|  | 5 nM | 50.3 ± 8.7 |
|  | 10 nM | 69.0 ± 5.5 |
|  | 30 nM | 91.0 ± 1.4 |
|  | 100 nM | 96.0 ± 1.6 |
|  | 300 nM | 96.0 ± 1.6 |
|  | 1 μM | 96.6 ± 1.6 |
| R(−)DMS | 100 nM | 14.3 ± 3.6 |
|  | 300 nM | 42.1 ± 4.0 |
|  | 1 μM | 76.9 ± 1.47 |
|  | 3 μM | 94.4 ± 1.4 |
|  | 10 μM | 95.8 ± 1.4 |
|  | 3 μM | 95.7 ± 2.3 |
| S(+)DMS | 300 nM | 6.4 ± 2.8 |
|  | 1 μM | 11.1 ± 1.0 |

TABLE 5-continued

MAO-B Inhibition in Human Platelets Concentration

| Agent | Concentration | % Inhibition 0 ± SEM |
|---|---|---|
| | 3 μM | 26.6 ± 1.9 |
| | 10 μM | 42.3 ± 2.3 |
| | 30 μM | 68.2 ± 2.34 |
| | 100 μm | 83.7 ± 0.77 |
| | 1 mM | 94.2 ± 1.36 |

TABLE 6

MAO-B Inhibition in Guinea Pig Hippocampus

| Agent | Concentration | % Inhibition 0 ± SEM |
|---|---|---|
| Selegiline | 0.3 μM | 28.3 ± 8.7 |
| | 5 nM | 81.2 ± 2.6 |
| | 10 nM | 95.6 ± 1.3 |
| | 30 nM | 98.5 ± 0.5 |
| | 100 nM | 98.8 ± 0.5 |
| | 300 nM | 98.8 ± 0.5 |
| | 1 μM | 99.1 ± 0.45 |
| R(−)DMS | 100 nM | 59.4 ± 9.6 |
| | 300 nM | 86.2 ± 4.7 |
| | 1 μM | 98.2 ± 0.7 |
| | 3 μM | 98.4 ± 0.95 |
| | 10 μm | 99.1 ± 0.45 |
| | 30 μM | 99.3 ± 0.40 |
| S(+)DMS | 300 nM | 18.7 ± 2.1 |
| | 1 μM | 44.4 ± 6.4 |
| | 3 μM | 77.1 ± 6.0 |
| | 10 μM | 94.2 ± 1.9 |
| | 30 μM | 98.3 ± 0.6 |
| | 100 μM | 99.3 ± 0.2 |
| | 1 μm | 99.9 ± 0.1 |

TABLE 7

$IC_{50}$ Values for the Inhibition of MAO-B Guinea Pig

| Treatment | Human Platelets | Guinea Pig Hippocampal Cortex |
|---|---|---|
| Selegiline | 5 nM(1) | 1 nM (1) |
| R(−)DMS | 400 nM (80) | 60 nM (60) |
| S(+)DMS | 1400 nM (2800) | 1200 nM (1200) |

() = reduction in potency compared to selegiline

As observed, R(−)DMS was 20–35 times more potent than S(+)DMS as an MAO-B inhibitor and both enantiomers were less potent than selegiline.

MAO-A Inhibitory Activity In Vitro

Results obtained from experiments examining the inhibition of MAO-A in guinea pig hippocampus are summarized in Table 8. The $IC_{50}$ values for the two enantiomers of DMS and for selegiline are shown in Table 9.

TABLE 8

MAO-A Inhibition in Guinea Pig Hippocampus

| Agent | Concentration | % Reduction 0 ± SEM |
|---|---|---|
| Selegiline | 300 nM | 11.95 ± 2.4 |
| | 1 μM | 22.1 ± 1.2 |
| | 3 μM | 53.5 ± 2.7 |
| | 10 μM | 91.2 ± 1.16 |
| | 100 μM | 98.1 ± 1.4 |
| | 1 mM | 99.8 ± 0.2 |
| R(−)DMS | 300 nM | 4.8 ± 2.1 |
| | 1 μM | 4.2 ± 1.5 |
| | 3 μM | 10.5 ± 2.0 |
| | 10 μM | 19.0 ± 1.3 |
| | 100 μM | 64.2 ± 1.5 |
| | 1 mM | 96.5 ± 1.2 |
| S(+)DMS | 1 μM | 3.3 ± 1.5 |
| | 3 μM | 4.3 ± 1.0 |
| | 10 μM | 10.5 ± 1.47 |
| | 100 μM | 48.4 ± 1.8 |
| | 1 nM | 92.7 ± 2.5 |
| | 10 nM | 99.6 ± 0.35 |

TABLE 9

$IC_{50}$ Values for the Inhibition of MAO-A

| Treatment | $IC_{50}$ for MAO-A in Guinea Pig Hippocampal Cortex |
|---|---|
| Selegiline | 2.5 μM (1) |
| R(−)DMS | 50.0 μM (20) |
| S(+)DMS | 100.0 μM (40) |

() = reduction in potency compared to selegiline

R(−)DMS was twice as potent as S(+)DMS as an MAO-A inhibitor and both were 20–40 times less potent than selegiline. Moreover, each of these agents were 2–3 orders of magnitude, i.e., 100 to 1000 times, less potent as inhibitors of MAO-A than inhibitors of MAO-B in hippocampal brain tissue. Therefore, selegiline and each enantiomer of DMS can be classified as selective MAO-B inhibitors in brain tissue.

Results of In Vivo Experiments

Figure 11:
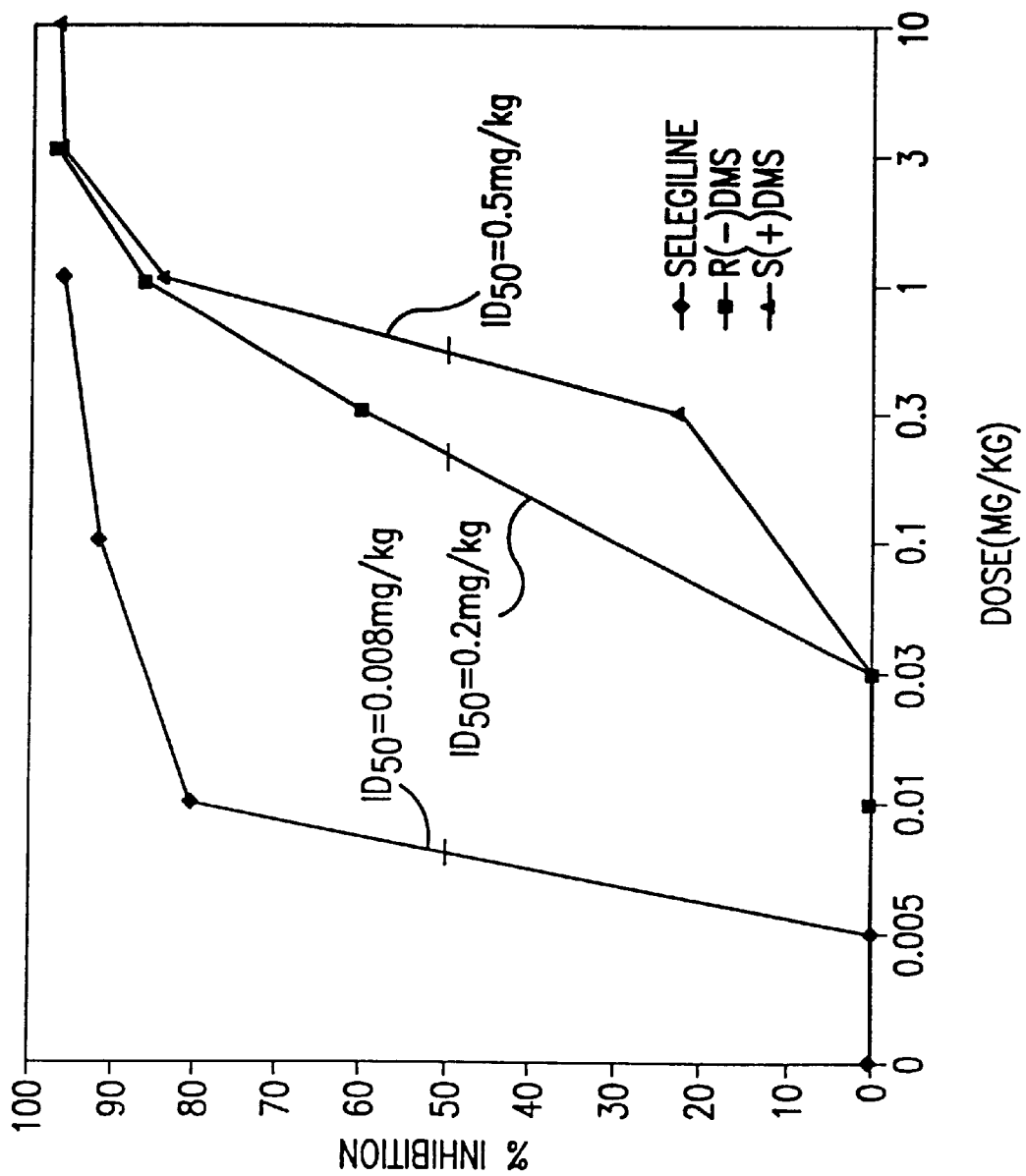
FIG. 11: In vivo MAO-B Inhibition in Guinea Pig Hippocampus. Various doses of selegiline, R(−) desmethylselegiline, and S(+) desmethylselegiline were administered daily to guinea pigs for a period of 5 days. Animals were then sacrificed and the MAO-B activity in the hippocampus portion of the brain was determined. Results were expressed as a percent inhibition relative to hippocampus MAO-B activity in control animals and are shown in FIG. 11. The plots were used to estimate the $ID_{50}$ dosage for each agent. The $ID_{50}$ for selegiline was about 0.008 mg/kg; for R(−)DMS, it was about 0.2 mg/kg; and for S(+)DMS, it was about 0.5 mg/kg.

Each enantiomer of DMS was administered in vivo by subcutaneous injection once a day for five consecutive days, and inhibition of brain MAO-B activity was then determined. In preliminary studies, selegiline was found to have an $ID_{50}$ of 0.03 mg/kg; and both R(−)DMS and S(+)DMS were determined to be about 10 times less potent. More recent studies, performed on a larger group of animals, indicates that R(−)DMS is actually about 25 times less potent than selegiline as an inhibitor of MAO-B and that S(+)DMS is about 50 times less potent. Results are shown in FIG. 11 and $ID_{50}$ values are summarized in Table 10.

TABLE 10

$ID_{50}$ Values for Brain MAO-B Following 5 Days of Administration

| Treatment | $ID_{50}$ for MAO-B in Guinea Pig Hippocampal Cortex |
|---|---|
| Selegiline | 0.008 mg/kg (1) |
| R(−)DMS | 0.20 mg/kg (25) |
| S(+)DMS | 0.50 mg/kg (60) |

()-reduction in potency compared to selegiline

This experiment demonstrates that the enantiomers of DMS penetrate the blood brain-barrier and inhibit brain MAO-B after in vivo administration. It also demonstrates that the potency differences as an MAO-B inhibitor observed in vitro between each of the DMS enantiomers and selegiline are substantially reduced under in vivo conditions.

In experiments examining the effect of 5 s.c. treatments on MAO-A activity in guinea pig cortex (hippocampus), it was found that selegiline administration at a dose of 1.0 mg/kg resulted in a 36.1% inhibition of activity. R(−)DMS resulted in an inhibition of 29.8% when administered at a dose of 3.0 mg/kg. S(+)DMS administration did not cause any observable inhibition at the highest dose tested (10 mg/kg) indicating that it has significantly less cross reactivity potential.

C. Conclusions

In vitro, R(−)DMS and S(+)DMS both exhibit activity as MAO-B and MAO-A inhibitors. Each enantiomer was selective for MAO-B. S(+)DMS was less potent than R(−)DMS and both enantiomers of DMS were less potent than selegiline in inhibiting both MAO-A and MAO-B.

In vivo, both enantiomers demonstrated activity in inhibiting MAO-B, indicating that these enantiomers are able to cross the blood-brain barrier. The ability of these agents to inhibit MAO-B suggests that these agents may be of value as therapeutics for hypodopaminergic diseases such as ADHD and dementia.

EXAMPLE 6

Immune System Restoration by R(−)DMS and S(+)DMS

There is an age-related decline in immunological function that occurs in animals and humans which makes older individuals more susceptible to infectious disease and cancer. U.S. Pat. Nos. 5,276,057 and 5,387,615 suggest that selegiline is useful in the treatment of immune system dysfunction. The present experiments were undertaken to determine whether R(−)DMS and S(+) are also useful in the treatment of such dysfunction. It should be recognized that an ability to bolster a patient's normal immunological defense's would be beneficial in the treatment of a wide variety of acute and chronic diseases including cancer, AIDS, and both bacterial and viral infections.

A. Test Procedure

The present experiments utilized a rat model to examine the ability of R(−)DMS and S(+)DMS to restore immunological function. Rats were divided into the following experimental groups:

1) young rats (3 months old, no treatment);
2) old rats (18–20 months old, no treatment);
3) old rats injected with saline;
4) old rats treated with selegiline at a dosage of 0.25 mg/kg body weight;
5) old rats treated with selegiline at a dosage of 1.0 mg/kg body weight;
6) old rats treated with R(−)DMS at a dosage of 0.025 mg/kg body weight;
7) old rats treated with R(−)DMS at a dosage of 0.25 mg/kg body weight;
8) old rats treated with R(−)DMS at a dosage of 1.0 mg/kg body weight;
9) old rats treated with S(+)DMS at a dosage of 1.0 mg/kg body weight.

Rats were administered saline or test agent ip, daily for 60 days. They were then maintained for an additional "wash out" period of 10 days during which time no treatment was given. At the end of this time, animals were sacrificed and their spleens were removed. The spleen cells were then assayed for a variety of factors which are indicative of immune system function. Specifically, standard tests were employed to determine the following:

1) in vitro production of γ-interferon by concanavalin A-stimulated spleen cells;
2) in vitro concanavalin A-induced production of interleukin-2;
3) percentage of IgM positive spleen cells (IgM is a marker of B lymphocytes);
4) percentage of CD5 positive spleen cells (CD5 is a marker of T lymphocytes).

B. Results

The effect of administration of selegiline, R(−)DMS and S(+)DMS on concanavalin A-induced interferon production by rat spleen cells is shown in Tables 11 and 12. Table 11 shows, that there is a sharp decline in cellular interferon production that occurs with age. Administration of selegiline, R(−)DMS and S(+)DMS all led to a restoration of γ-interferon levels with the most dramatic increases occurring at dosages of 1.0 mg/kg body weight.

TABLE 11

Effect of Age on T Cell Function*

| Groups | IL-2 | | IFN-γ | |
|---|---|---|---|---|
| | U/ml | std. error | U/ml | std. error |
| young | 59.4 | 18.27 | 12297 | 6447 |
| old | 19.6 | 7.52 | 338 | 135 |

*T cell activities were assessed after stimulation of rat spleen cells with concanavalin A. TH, cytokines, IL-2 and IFN-γ were measured. Young vs. old, p = 0.0004

TABLE 12

Mean and % control IL-2 and IFN g

| | IL-2 U/ml | | IFN-γ U/ml | |
|---|---|---|---|---|
| Groups | mean | % control | mean | % control |
| control* | 19.64 | 100 | 351 | 100 |
| control | 41.22 | 210 | 339 | 96 |
| R(−)DMS | 55.17 | 281 | 573 | 163 |
| R(−)DMS | 64.54 | 329 | 516 | 147 |
| R(−)DMS | 43.7 | 223 | 2728 | 777 |
| S(+)DMS | 57.12 | 291 | 918 | 261 |
| Sel 0.25 | 109.6 | 558 | 795 | 226 |
| Sel. 1.0 | 73.78 | 376 | 1934 | 550 |

*Old rats (22 months old) with no treatment

Table 12 shows the extent to which R(−)DMS, S(+)DMS and selegiline are capable of restoring γ-interferon production in the spleen cells of old rats. Interferon-γ is a cytokine associated with T cells that inhibit viral replication and regulate a variety of immunological functions. It influences the class of antibodies produced by B-cells, upregulates class I and class II MHC complex antigens and increases the efficiency of macrophage-mediated killing of intracellular parasites.

Histological immunofluorescence studies show a dramatic loss of innervation in rat spleens with age. When rats are treated with R(−)DMS, there is a significant increase in innervation in the spleens of animals and this increase occurs in a dose-response manner. S(+)DMS did not show any effect on histological examination, despite a modest increase in interferon-γ production. IL-2 production was not enhanced by treatment with R(−)DMS or S(+)DMS, suggesting that the effects of these agents may be limited to IFN-γ production.

C. Conclusions

The results obtained with respect to histological examination, the production of interferon, and the percentage of IgM positive spleen cells support the conclusion that the DMS enantiomers are capable of at least partially restoring the age-dependent loss of immune system function. The results observed with respect to IFN-γ are particularly important. In both humans and animals, IFN-y production is associated with the ability to successfully recover from infection with viruses and other pathogens. In addition, it appears that R(–)DMS and S(+)DMS will have a therapeutically beneficial effect for diseases and conditions mediated by weakened host immunity. This would include AIDS, response to vaccines, infectious diseases and adverse immunological effects caused by cancer chemotherapy and cancer.

EXAMPLE 7

Examples of Dosage Forms

A. Desmethylselegiline Patch.

| Dry Weight Basis Component | (mg/cm$^2$) |
|---|---|
| Durotak ® 87-2194 adhesive acrylic polymer | 90 parts by weight |
| Desmethylselegiline | 10 parts by weight |

The two ingredients are thoroughly mixed, cast on a film backing sheet (e.g., Scotchpak® 9723 polyester) and dried. The backing sheet is cut into patches a fluoropolymer release liner (e.g., Scotchpak® 1022) is applied, and the patch is hermetically sealed in a foil pouch. One patch is applied daily to supply 1–10 mg of desmethylselegiline per 24 hours in the treatment of conditions in a human produced by neuronal degeneration or neuronal trauma.

B. Ophthalmic Solution

Desmethylselegiline (0.1 g) as the hydrochloride, 1.9 g of boric acid, and 0.004 g of phenyl mercuric nitrate are dissolved in sterile water qs 100 ml. The mixture is sterilized and sealed. It can be used ophthalmologically in the treatment of conditions produced by neuronal degeneration or neuronal trauma, as for example glaucomatous optic neuropathy and macular degeneration.

C. Intravenous Solution.

A 1% solution is prepared by dissolving 1 g of desmethylselegiline as the HCl in sufficient 0.9% isotonic saline solution to provide a final volume of 100 ml. The solution is buffered to pH 4 with citric acid, sealed, and sterilized to provide a 1% solution suitable for intravenous administration in the treatment of conditions produced by neuronal degeneration or neuronal trauma.

D. Oral Dosage Form

Tablets and capsules containing desmethylselegiline are prepared from the following ingredients (mg/unit dose):

| desmethylselegiline | 1–5 |
|---|---|
| microcrystalline cellulose | 86 |
| lactose | 41.6 |
| citric acid | 0.5–2 |
| sodium citrate | 0.1–2 |
| magnesium stearate | 0.4 | with an approximately 1:1 ratio of citric acid and sodium citrate.

EXAMPLE 8

Treatment of Breast Cancer

A patient with breast cancer will be treated with a pharmaceutical composition that includes R(–)DMS, S(+)DMS, or a mixture of both (10 mg per day), as well as paclitaxel, by intravenous administration. Paclitaxel will be administered at a dose of 175 mg/m$^2$ over a period of 3 hours. Treatment will be repeated every 3 weeks for a total of ten cycles. Administration of R(–)DMS, S(+)DMS, or the mixture of both may be continued for at least one month after treatment with paclitaxel ends. During the course of treatment, a physician will evaluate tumor response and reoccurrence in the patient on a weekly, monthly, or yearly basis.

Additionally, patients at risk for developing breast cancer due to family history, genotype, age, or previous occurrence will be treated with a pharmaceutical composition that includes R(–)DMS, S(+)DMS, or a mixture of both R(–)DMS and S(+)DMS. R(–)DMS, S(+)DMS, or a mixture of both is administered to a patient at risk for breast cancer via a transdermal patch at a delivered dose of about 0.05 to 0.10 mg/kg per day for an extended period of time. The preventive therapy utilizing DMS may be continued for months or years, depending on the risk factors for the patient, including age. While a patient is being treated with DMS, evaluations of tumor occurrence, reoccurrence, or progression, as well as toxic side effects, may be carried out by a physician on a weekly, monthly, or yearly basis. Treatment may be continued for a period extending as long as a beneficial effect on suppression, inhibition, or prevention of tumor formation or progression is obtained or until the presentation of unacceptable side effects.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing: from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for obtaining a selegiline therapeutic effect in a patient with a neoplastic disease or condition, comprising administering to the patient R(–)DMS in a dosage regimen effective to inhibit, in whole or in part, occurrence or progression of the neoplastic disease or condition.

2. The method of claim 1, wherein the R(–)DMS is in a substantially enantiomerically pure form.

3. The method of claim 1, wherein the R(–)DMS is administered as the free base.

4. The method of claim 1, wherein the R(–)DMS is administered as an acid addition salt.

5. The method of claim 4, wherein the acid addition salt is hydrochloride salt.

6. The method of claim 1, wherein the neoplastic disease or condition is a mammary tumor or a pituitary tumor.

7. The method of claim 1, wherein the R(–)DMS is administered at a daily dose of between about 0.02 mg/kg and about 5.0 mg/kg, calculated on the basis of the free secondary amine.

8. The method of claim 1, wherein the R(−)DMS is administered at a daily dose of between about 0.6 mg/kg and about 0.8 mg/kg, calculated on the basis of the free secondary amine.

9. The method of claim 1, wherein the R(−)DMS is administered by an oral route of administration.

10. The method of claim 1, wherein the R(−)DMS is administered by a non-oral route of administration.

11. The method of claim 1, wherein the R(−)DMS is administered sublingually, buccally, or parenterally.

12. The method of claim 1, wherein the R(−)DMS is administered by a transdermal patch.

13. The method of claim 1, wherein the patient is a human.

14. A pharmaceutical composition, comprising:
   a) R(−)DMS; and
   b) a second therapeutic agent useful in the treatment of a neoplastic disease or condition.

15. The composition of claim 14, wherein the second therapeutic agent is an anti-neoplastic agent.

16. The composition of claim 15, wherein the anti-neoplastic agent is tamoxifen, cisplatin, paclitaxel, or methotrexate.

17. The composition of claim 14, wherein the second therapeutic agent is a radiation implant.

18. The composition of claim 14, wherein between about 0.02 and about 5.0 mg/kg of R(−)DMS, calculated on the basis of the free secondary amine, is in a unit dose of the composition.

19. The composition of claim 14, wherein between about 0.6 and about 0.8 mg/kg of R(−)DMS, calculated on the basis of the free secondary amine, is in a unit dose of the composition.

20. The composition of claim 14, wherein between about 1.0 mg and about 100.0 mg of R(−)DMS is in a unit dose of the composition.

21. The composition of claim 14, wherein between about 5.0 mg and about 10.0 mg of R(−)DMS is in a unit dose of the composition.

22. The composition of claim 14, for oral administration.

23. The composition of claim 14, for non-oral administration.

24. The composition of claim 14, for transdermal administration.

25. The composition of claim 14, wherein the composition is a transdermal patch.

26. A method for obtaining a selegiline therapeutic effect in a patient with a neoplastic disease or condition, comprising administering to the patient a pharmaceutical composition comprising:
   a) R(−)DMS; and
   b) a second therapeutic agent useful in the treatment of a neoplastic disease or condition;

wherein one or more unit doses of the composition are effective to inhibit, in whole or in part, occurrence or progression of the neoplastic disease or condition.

* * * * *

UNITED STATES PATENT AND TRADEMARK OFFICE
CERTIFICATE OF CORRECTION

PATENT NO.    : 6,528,082 B2  
DATED         : March 4, 2003  
INVENTOR(S)   : Cheryl D. Blume and Anthony R. DiSanto Page 1 of 1

It is certified that error appears in the above-identified patent and that said Letters Patent is hereby corrected as shown below:

<u>Title page,</u>  
Item [63], Related U.S. Application Data, please replace paragraph with paragraph shown below:  
-- Continuation-in-part of application No. 09/448,483, filed on Nov. 24, 1999, now Pat. No. 6,210,706, which is a divisional of 08/679,328, filed on Jul. 12, 1996, now Pat. No. 6,033,682, and application No. 08/679,330, filed on Jul. 12, 1996, now Pat. No. 6,348,208, which are continuations-in-part of application No. PCT/US96/01561, filed on Jan. 11, 1996 and application No. 08/372,139, filed on Jan. 13, 1995. --

Signed and Sealed this

Twenty-fourth Day of June, 2003

JAMES E. ROGAN  
*Director of the United States Patent and Trademark Office*